United States Patent
Yamamoto et al.

(10) Patent No.: US 7,022,855 B2
(45) Date of Patent: Apr. 4, 2006

(54) HALOGEN-SUBSTITUTED QUINOLINE DERIVATIVES AND ECTOPARASITE CONTROL AGENT

(75) Inventors: Kazumi Yamamoto, Yokohama (JP); Kazuhiko Oyama, Yokohama (JP); Masayo Sakai, Yokohama (JP); Ryo Horikoshi, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 10/681,192

(22) Filed: Oct. 9, 2003

(65) Prior Publication Data

US 2004/0087618 A1    May 6, 2004

Related U.S. Application Data

(63) Continuation of application No. PCT/JP02/03685, filed on Apr. 12, 2002.

(30) Foreign Application Priority Data

Apr. 12, 2001   (JP) .............................. 2001-114459

(51) Int. Cl.
*C07D 221/06*  (2006.01)
*C07D 219/04*  (2006.01)
*C07D 215/16*  (2006.01)

(52) U.S. Cl. ................. 546/79; 546/103; 546/156; 546/159

(58) Field of Classification Search ................. 546/79, 546/103, 156, 159
See application file for complete search history.

(56) References Cited

U.S. PATENT DOCUMENTS 5,190,952 A * 3/1993 Minowa et al. ............. 514/297
5,194,617 A   3/1993 Minowa et al.

FOREIGN PATENT DOCUMENTS

EP           407192 A2       1/1991
EP           407192 B1       1/1991
JP        2003-041004        2/1991
JP        2001-097866        4/2001
WO       WO 96/36608 A1     11/1996
WO          02/26713 A1      4/2002

OTHER PUBLICATIONS

Minowa, CA 127:201395, abstract of Bioscience, Biotechnology and Biochemistry, vol. 61(7), pp1213-1215, 1997.*
Minowa, Nobuto et al., "Synthesis and insecticidal activity of new 2- and 6-substituted 4-acetoxyquinolines", Bioscience, Biotechnology, and Biochemistry, 1997, pp. 1213 to 1215, vol. 61, No. 7.

* cited by examiner

*Primary Examiner*—D. Margaret Seaman
(74) *Attorney, Agent, or Firm*—Heller Ehrman LLP

(57) ABSTRACT

An objective of the present invention is to provide an ectoparasite control agent for homothermic animals, which has high control effect and is safe. The compounds according to the present invention are compounds represented by formula (I) and salts thereof:

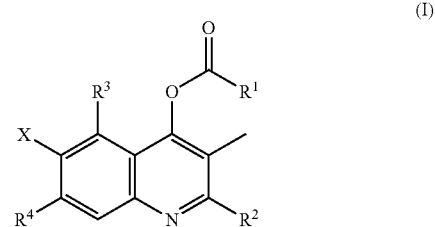

(I)

wherein $R^1$ represents optionally substituted alkyl; optionally substituted alkenyl; optionally substituted alkynyl; $OR^5$ wherein $R^5$ represents optionally substituted alkyl, optionally substituted alkenyl, or optionally substituted alkynyl; or $SR^5$ wherein $R^5$ is as defined above, $R^2$ represents optionally substituted alkyl, any one of $R^3$ and $R^4$ represents hydrogen and the other represents fluorine, chlorine, bromine, or $CF_3$, and X represents fluorine or chlorine.

7 Claims, No Drawings

HALOGEN-SUBSTITUTED QUINOLINE DERIVATIVES AND ECTOPARASITE CONTROL AGENT

This application is a continuation of Application No. PCT/JP02/03685, filed Apr. 12, 2002, which claims priority to Japanese Application No. 2001-114459, filed Apr. 12, 2001. The entirety of these applications is hereby incorporated by reference.

BACKGROUND OF THE INVENTION

1. Field of the Invention

The present invention relates to novel halogen-substituted quinoline derivatives and an ectoparasite control agent comprising the same as active ingredient.

2. Related Art

Ectoparasites parasitic on mammals and birds induce symptoms such as malnutrition, weakness, weight reduction, and decrease in an egg laying rate. A large number of control agents have hitherto been developed for these ectoparasites. In recent years, however, for example, a lowering in sensitivity of the ectoparasites to drugs is serious, and novel drugs, which have high control effect and are safe, have been desired. Japanese Patent No. 2633377 discloses quinoline derivatives as insecticides for agricultural and horitircultural purposes, but on the other hand, does not disclose control of harmful organisms parasitic on homothermic animals.

SUMMARY OF THE INVENTION

The present inventors have now found that 4-acyloxyquinoline derivatives have excellent control effect against ectoparasites of mammals and birds.

Accordingly, an object of the present invention is to provide an ectoparasite control agent for homothermic animals which has high control effect and is safe.

The compounds according to the present invention are compounds represented by formula (I) and salts thereof:

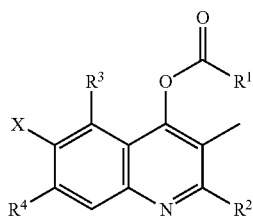

wherein $R^1$ represents alkyl having 1 to 6 carbon atoms optionally substituted by a halogen atom or cyano; alkenyl having 2 to 6 carbon atoms optionally substituted by a halogen atom or cyano; alkynyl having 2 to 6 carbon atoms optionally substituted by a halogen atom or cyano; group —O—$R^5$ wherein $R^5$ represents alkyl having 1 to 6 carbon atoms optionally substituted by a halogen atom or cyano, alkenyl having 2 to 6 carbon atoms optionally substituted by a halogen atom or cyano, or alkynyl having 2 to 6 carbon atoms optionally substituted by a halogen atom or cyano; or group —S—$R^5$ wherein $R^5$ is as defined above, $R^2$ represents alkyl having 1 to 4 carbon atoms optionally substituted by a halogen atom, any one of $R^3$ and $R^4$ represents a hydrogen atom and the other represents a fluorine atom, a chlorine atom, a bromine atom, or —$CF_3$, and X represents a fluorine atom or a chlorine atom.

According to the present invention, there is provided an ectoparasite control agent for mammals and birds, comprising the compound according to the present invention.

Further, according to the present invention, there is provided an ectoparasite control agent for mammals and birds, comprising a compound represented by formula (100) or a salt thereof:

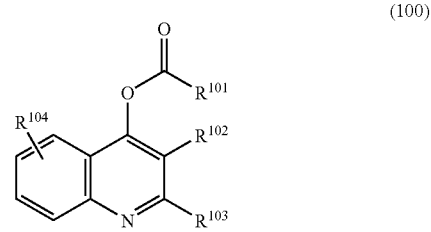

wherein $R^{101}$ represents a hydrogen atom; alkyl having 1 to 18 carbon atoms; alkenyl having 2 to 18 carbon atoms; cycloalkyl having 3 to 10 carbon atoms, which is optionally substituted by a halogen atom, alkyl having 1 to 4 carbon atoms, or alkenyl having 2 to 4 carbon atoms; alkyl having 1 to 4 carbon atoms substituted by phenyl; alkyl having 1 to 4 carbon atoms substituted by phenoxy; aryl; —O—$R^{105}$ wherein $R^{105}$ represents alkyl having 1 to 4 carbon atoms or aryl; or

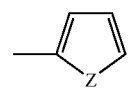

wherein Z represents —S— or —O—, $R^{102}$ represents a hydrogen atom or alkyl having 1 to 4 carbon atoms, $R^{103}$ represents alkyl having 1 to 10 carbon atoms or alkenyl having 2 to 4 carbon atoms, or $R^{102}$ and $R^{103}$ together form —$(CH_2)_m$— wherein m is 3 or 4, provided that, when $R^{102}$ represents a hydrogen atoms and $R^{103}$ represents methyl, $R^{101}$ does not represent —O—$R^{105}$, and $R^{104}$ represents a hydrogen atom; one to four halogen atoms, which may be the same or different; alkyl having 1 to 4 carbon atoms; or alkoxy having 1 to 4 carbon atoms, provided that, when $R^{101}$ represents methyl, $R^{102}$, $R^{103}$, and $R^{104}$ do not represent a hydrogen atom.

DETAILED DESCRIPTION OF THE INVENTION

The term "halogen atom" as used herein means a fluorine, chlorine, bromine, or iodine atom, preferably a fluorine or chlorine atom.

The term "alkyl" as used herein means straight chain alkyl, branched chain alkyl, or cyclo (cyclic) alkyl. Examples of alkyl include: straight chain alkyl such as methyl, ethyl, propyl, butyl, pentyl, and hexyl; branched chain alkyl such as isopropyl, isobutyl, s-butyl, t-butyl, neopentyl, isopentyl, and isohexyl; and cycloalkyl such as cyclopropyl, 1-methylcyclopropyl, cyclopropylmethyl, cyclobutyl, cyclopentyl, and cyclohexyl.

The term "alkoxy" as used herein means straight chain alkoxy, branched chain alkoxy, or cycloalkoxy. Examples of alkoxy include: straight chain alkoxy such as methoxy, ethoxy, propoxy, and butoxy; branched chain alkoxy such as isopropoxy, isobutoxy, s-butoxy, and t-butoxy; and cycloalkoxy such as cyclopropoxy, 1-methylcyclopropoxy, cyclopropylmethoxy, and cyclobutyloxy.

The term "alkenyl" as used herein means straight chain alkenyl, branched chain alkenyl, or cycloalkenyl. Examples of alkenyl include vinyl, allyl, propenyl, isopropenyl, butenyl, 2-butenyl, 3-butenyl, 2-methyl-1-propenyl, 2-methylallyl, pentenyl, 2-pentenyl, 3-pentenyl, 4-pentenyl, cyclopentenyl, hexenyl, 2-hexenyl, 3-hexenyl, 4-hexenyl, 5-hexenyl, and cyclohexenyl.

The term "alkynyl" as used herein means straight chain alkynyl, branched chain alkynyl, or cycloalkynyl. Examples of alkynyl include ethynyl, propynyl, 2-propynyl, butynyl, 2-butynyl, 3-butynyl, pentynyl, 2-pentynyl, 3-pentynyl, 4-pentynyl, hexynyl, 2-hexynyl, 3-hexynyl, 4-hexynyl, and 5-hexynyl.

Alkyl having 1 to 6 carbon atoms is preferably alkyl having 1 to 4 carbon atoms.

Alkyl having 1 to 10 carbon atoms is preferably alkyl having 1 to 6 carbon atoms.

Alkyl having 1 to 18 carbon atoms is preferably alkyl having 1 to 12 or 1 to 6 carbon atoms.

Cycloalkyl having 3 to 10 carbon atoms is preferably cycloalkyl having 3 to 8 or 3 to 6 carbon atoms.

Alkenyl having 2 to 6 carbon atoms is preferably alkenyl having 2 to 4 carbon atoms.

Alkenyl having 2 to 18 carbon atoms is preferably alkenyl having 2 to 12 or 2 to 6 carbon atoms.

Alkynyl having 2 to 6 carbon atoms is preferably alkynyl having 2 to 4 carbon atoms. The The term "aryl" as used herein preferably refers to phenyl optionally substituted by alkyl having 1 to 4 carbon atoms and/or a halogen atom or naphthyl optionally substituted by alkyl having 1 to 4 carbon atoms and/or a halogen atom.

Examples of preferred compounds according to the present invention are compounds represented by formula (I) wherein any one of $R^3$ and $R^4$ represents a hydrogen atom and the other represents a fluorine or chlorine atom.

The compounds according to the present invention are preferably compounds represented by formula (Ia):

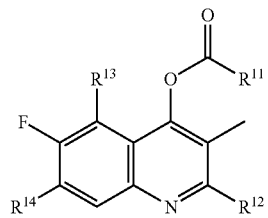

(Ia)

wherein $R^{11}$ represents alkyl having 1 to 4 carbon atoms optionally substituted by a halogen atom or alkoxy having 1 to 4 carbon atoms optionally substituted by a halogen atom; $R^{12}$ represents alkyl having 1 to 4 carbon atoms optionally substituted by a halogen atom; and any one of $R^{13}$ and $R^{14}$ represents a hydrogen atom and the other represents a fluorine or chlorine atom.

Examples of preferred compounds according to the present invention are compounds 1 to 81 described in working examples.

Examples of particularly preferred compounds according to the present invention are the following compounds:

Compound 2: 2-ethyl-3-methyl-4-cyclopropanecarbonyloxy-5,6-difluoroquinoline;

Compound 19: 2-ethyl-3-methyl-4-acetyloxy-5-chloro-6-fluoroquinoline;

Compound 24: 2-ethyl-3-methyl-4-methoxycarbonyloxy-5,6-difluoroquinoline;

Compound 25: 2,3-dimethyl-4-methoxycarbonyloxy-5,6-difluoroquinoline;

Compound 39: 2-ethyl-3-methyl-4-methanethiolcarbonyloxy-5,6-difluoroquinoline;

Compound 41: 2-ethyl-3-methyl-4-propargyloxycarbonyloxy-5,6-difluoroquinoline;

Compound 44: 2,3-dimethyl-4-acetoxy-5,6-difluoroquinoline;

Compound 46: 2,3-dimethyl-4-methanethiolcarbonyloxy-5,6-difluoroquinoline;

Compound 50: 2,3-dimethyl-4-propargyloxycarbonyloxy-5,6-difluoroquinoline;

Compound 52: 2,3-dimethyl-4-(3-butynyl)oxycarbonyloxy-5,6-difluoroquinoline;

Compound 56: 2-ethyl-3-methyl-4-(3-butynyl)oxycarbonyloxy-5,6-difluoroquinoline;

Compound 57: 2,3-dimethyl-4-allyloxycarbonyloxy-5,6-difluoroquinoline;

Compound 65: 2,3-dimethyl-4-acetoxy-5,6-dichloroquinoline; and

Compound 67: 2,3-dimethyl-4-methoxycarbonyloxy-5,6-dichloroquinoline.

In the compounds represented by formula (100), $R^{104}$ preferably represents one or two halogen atoms, alkyl groups or alkoxy groups which may be the same or different.

The compounds represented by formula (I) and the compounds represented by formula (100) may form salts, and examples thereof include hydrochloric acid salts, nitric acid salts, phosphoric acid salts, and acetic acid salts.

The compounds represented by formula (I) and the compounds represented by formula (100) may be produced, for example, according to a method shown in scheme 1. For the production of these compounds, reference may be made to Japanese Patent Laid-Open No. 128355/1991.

Scheme 1

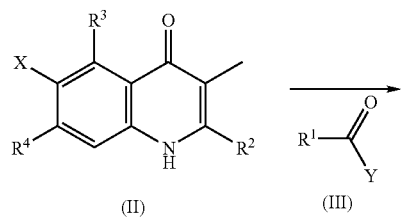

(II)     (III)

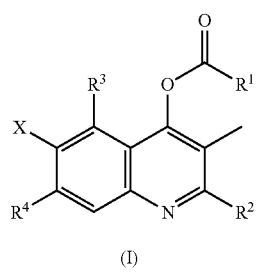

(I)

wherein Y represents a chlorine atom or hydroxyl; and $R^1$, $R^2$, $R^3$, $R^4$ and X are as defined in formula (I).

A compound represented by formula (I) can be synthesized by reacting a compound represented by formula (II) with a reagent represented by formula (III) in the absence of a solvent or in the presence of a suitable solvent. When Y represents a chlorine atom, the compound represented by formula (I) can be synthesized by carrying out the reaction in the presence of a suitable base, for example, an organic amine, such as triethylamine or pyridine, or an inorganic alkali, such as sodium carbonate, potassium carbonate, or sodium hydride. When Y represents hydroxyl, the compound represented by formula (I) can be synthesized by carrying out the reaction in the presence of a suitable condensing agent, for example, dicyclohexylcarbodiimide (DCC), 1-hydroxybenzotriazole (HOBt), or 2-chloro-1,3-dimethylimidazolinium chloride (DMC).

The reagent represented by formula (III) is preferably used in an amount in the range of 1 to 50 equivalents, preferably in the range of 1 to 10 equivalents, based on the compound represented by formula (II). Solvents usable herein are organic solvents inert to the reaction, for example, dimethylformamide, tetrahydrofuran, dimethyl sulfoxide, and dichloromethane. The reaction may be carried out at a temperature in the range of 0° C. to 140° C.

The compound represented by formula (II) as a start compound in scheme 1 may be produced according to a method shown in scheme 2. In the production of the compound represented by formula (II), reference may be made to J. Am. Chem. Soc. 70, 2402 (1948), Tetrahedron Lett. 27, 5323 (1986).

Specifically, the compound represented by formula (II) may be produced by imidating a halogen-substituted aniline, which may be synthesized by a conventional method or is commercially available, with a β-ketoester in the absence or presence of an acid catalyst in a suitable solvent, for example, benzene, toluene, or xylene, and further cyclizing the imide compound in the absence of a solvent or in the presence of a high-boiling solvent such as diphenyl ether or cyclizing the imide compound in a solvent such as toluene or xylene in the presence of an acid catalyst. Acid catalysts usable in the imidation and the cyclization include trifluoroboron etherate, p-toluenesulfonic acid, and polyphosphoric acid. The imidation and the cyclization may be carried out, if appropriate, in two steps in respective different solvents or the same solvent.

Scheme 2

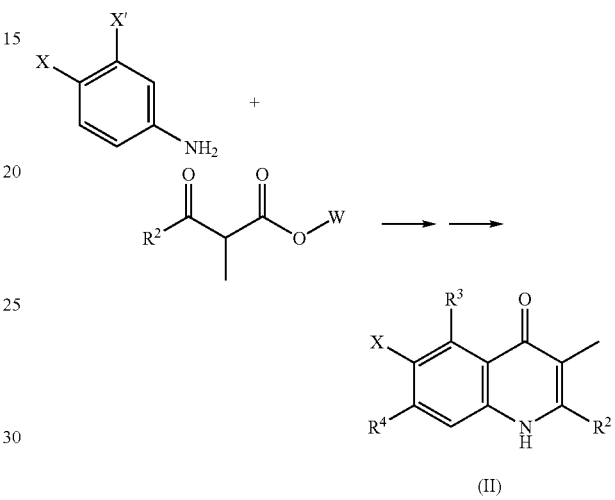

(II)

wherein $R^2$, $R^3$, $R^4$, and X are as defined in formula (I); X' represents a fluorine atom, a chlorine atom, a bromine atom, or $-CF_3$; and W represents methyl or ethyl.

As demonstrated in Test Examples 1 to 4, the compounds represented by formula (I) and the compounds represented by formula (100) had excellent control activity against ectoparasites parasitic on homotermic animals. Therefore, the compounds represented by formula (I) and the compounds represented by formula (100) can be used for controlling ectoparasites parasitic, for example, on mammals, such as humans, cattle, horses, pigs, sheep, goats, camels, donkeys, dogs, cats, rabbits, monkeys, guinea pigs, and hamsters, and birds such as chickens, ducks, gooses, and turkeys.

Ectoparasites include: Anoplura such as Haematopinus spp., Linognathus spp., Pediculus spp., and Phtirus spp.; Mallophaga such as Menopon spp., Eomenacanthus, Felicola spp., and Damalina spp.; Siphonaptera such as Ctenocephalides spp., Echidnophaga spp., and Pulex spp.; parasitic ticks such as Rhipicephalus spp., Haemaphysalis longicornis, Boophilus spp., Amblyomma spp., Dermacentor spp., Ixodes spp., Argas spp., and Ornithonyssus sylviarum; Mesostigmata such as Dermanyssus spp., Psoroptes spp., Sarcoptes spp., Notoedres spp., and Knemidocoptes spp.; and Diptera such as Chrysops spp., Tabanus spp., Stomoxys spp., Lucilia spp., Calliphora spp., Chrysomia spp., Sarcophaga spp., Gastrophilus spp., Oestrus spp., and Hippobosca spp.

These ectoparasites are sometimes parasitic in the body of mammals and birds. The compounds represented by formula (I) and the compounds represented by formula (100) may also be used for controlling parasites parasitic in the body.

In the control of ectoparasites of mammals and birds, an effective amount of one or more of the compounds represented by formula (I) or the compounds represented by formula (100), together with preparation additives, can be administered by oral administration; parenteral administration such as injection such as intramuscular, subcutaneous, intraveneous, or intraperitoneal injection; percutaneous administration such as dipping, spray, bathing, washing, pouring-on, spotting-on, and dusting; or nasal administration. Alternatively, the compounds represented by formula (I) and the compounds represented by formula (100) may be administered by shaped products using strips, plates, bands, collars, ear marks, limb bands, labeling devices or the like. For the administration, the compounds represented by formula (I) and the compounds represented by formula (100) may be formulated into suitable dosage forms according to the administration routes.

Suitable dosage forms which may be formulated include: solid preparations such as powders, granules, wettable powders, pellets, tablets, boluses, capsules, and shaped products containing active compounds; liquid preparations for injections, oral liquid preparations, and liquid preparations used on skins or in coeloms; solution preparations such as pour-on or spot-on preparations, floable preparations, and emulsions; and semi-solid preparations such as ointments and gels.

Solid preparations may be mainly used for oral administration or alternatively may be diluted with water or the like before percutaneous administration or environmental treatment. Solid preparations may be prepared by mixing the active compound with a suitable excipient, if necessary, after the addition of adjuvants and bringing the mixture into a desired shape. Suitable excipients include, for example, inorganic materials such as carbonates, hydrogencarbonates, phosphates, ammonium oxide, silica, and clay and organic materials such as saccharides, cellulose, ground grains, and starch.

Liquid preparations for injections may be intraveneously, intramuscularly, or subcutaneously administered. Liquid preparations for injections may be prepared by dissolving the active compound in a suitable solvent and optionally adding additives, such as a solubilizer, an acid, a base, a salt for buffering, an anitioxidant, and a protective agent, to the solution. Suitable solvents include water, ethanol, butanol, benzyl alcohol, glycerin, propylene glycol, polyethylene glycol, N-methylpyrrolidone, and mixtures of these solvents, physiologically acceptable vegetable oils, and synthetic oils for injections. Solubilizers include polyvinylpyrrolidone, polyoxyethylated castor oils, and polyoxyethylated sorbitan esters. Protective agents include benzyl alcohol, trichlorobutanol, p-hydroxybenzoic esters, and n-butanol.

Oral liquid preparations may be administered either directly or after dilution and may be prepared in the same manner as in the preparation of liquid preparations for injections.

Floable preparations, emulsions and the like may be administered percutaneously or by the environmental treatment either directly or after dilution.

Liquid preparations for use on the skin may be administered by pouring-on or spotting-on, spreading, rubbing-in, spray, or application, or immersion (dipping, bathing, or washing) for coating. They may be prepared in the same manner as in the preparation of liquid preparations for injections.

Pour-on and spot-on preparations may be dropped or sprayed on a limited site of the skin to allow the active compound to penetrate into the skin and thus to cause systemic action of the active compound. Pour-on and spot-on preparations may be prepared by dissolving, suspending, or emulsifying the active ingredient in a suitable solvent or solvent mixture compatible with the skin. If necessary, adjuvants such as surfactants, colorants, absorbefacients, antioxidants, photostabilizers, and adhesives may be added to the pour-on and spot-on preparations.

Suitable solvents include water, alkanols, glycols, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone, and 2,2-dimethyl-4-oxy-methylene-1,3-dioxolane. Absorbefacients include DMSO, isopropyl myristate, dipropylene glycol pelargonate, silicone oils, aliphatic esters, triglycerides, and fatty alcohols. Antioxidants include bisulfites, metabisulfites, ascorbic acid, butylhydroxytoluene, butylhydroxyanisole, and tocopherol.

Emulsions may be administered orally, percutaneously, or by injection. Emulsions may be prepared by dissolving the active ingredient in a hydrophobic phase or a hydrophilic phase and homogenizing the solution in other phase with the aid of a suitable emulsifier, if necessary, together with adjuvants such as a colorant, an absorbefacient, a protective agent, an antioxidant, a light-screening agent, and a thickening agent.

Hydrophobic phases (oils) include paraffin oils, silicone oils, sesame oils, almond oils, castor oils, synthetic triglyceride, ethyl stearate, di-n-butyryl adipate, hexyl laurylate, dipropylene glycol pelargonate, esters of branched short-chain fatty acids with saturated fatty acids having 16 to 18 carbon atoms, isopropyl myristate, isopropyl palmitate, esters of caprylic acid/capric acid with saturated fatty alcohols having 12 to 18 carbon atoms, isopropyl stearate, oleyl oleate, decyl oleate, ethyl oleate, ethyl lactate, waxy fatty esters, dibutyl phthalate, diisopropyl adipate, isotridecyl alcohol, 2-octyldodecanol, cetylstearyl alcohol, and oleyl alcohol.

Hydrophilic phases include water, propylene glycol, glycerin, and sorbitol.

Emulsifiers include: nonionic surfactants such as polyoxyethylated castor oils, polyoxyethylated monoolefinic acid sorbitan, sorbitan monostearate, glycerin monostearate, polyoxyethyl stearate, and alkylphenol polyglycol ether; amphoteric surfactants such as disodium N-lauryl-β-iminodipropionate and lecithin; anionic surfactants such as sodium laurylsulfate, fatty alcohol sulfuric acid ether, and monoethanolamine salt of mono-/dialkylpolyglycol orthophosphate; and cationic surfactants such as cetyltrimethylammonium chloride.

Other adjuvants include carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, wax, and colloidal silica.

Semi-solid preparations may be administered by coating or spreading on the skin or by introduction into the coelom. The gel may be prepared by adding a thickener, suitable for forming a transparent material having ointment-like viscous properties, to the solution prepared above in connection with liquid preparations for injections.

These preparations may be prepared by mixing with other insecticides, for example, organophosphorus insecticides, carbamate insecticides, or pyrethroid insecticides.

According to the present invention, there is provided use of the compound represented by formula (I) or a salt thereof or the compound represented by formula (100) or a salt thereof, for the manufacture of an ectoparasite control agent for mammals and birds.

Further, according to the present invention, there is provided a method for controlling an ectoparasite for mammals and birds, comprising the step of administering an effective amount of the compound represented by formula (I) or a salt thereof or the compound represented by formula (100) or a salt thereof to a mammal or a bird.

EXAMPLES

The present invention is further illustrated by the following Examples that are not intended as a limitation of the invention.

Example 1

2-Ethyl-3-methyl-4-cyclopropanecarbonyloxy-6,7-difluoroquinoline (compound 1) and 2-ethyl-3-methyl-4-cyclopropanecarbonyloxy-5,6-difluoroguinoline (compound 2)

3,4-Difluoroaniline (3.18 g) and 3.9 g of ethyl-2-methylpropionyl acetate were refluxed in toluene (50 ml) in the presence of 0.3 ml of boron trifluoride etherate for 3 hr. The reaction mixture was washed with a saturated sodium hydrogencarbonate solution and saturated brine and was dried over anhydrous sodium sulfate, and the solvent was then removed by evaporation. The resultant intermediate was refluxed in diphenyl ether for 30 min and was allowed to stand for cooling. The precipitate was then collected by filtration under the reduced pressure to give 1.9 g of a mixture of 2-ethyl-3-methyl-4-hydroxy-6,7-difluoroquinoline with 2-ethyl-3-methyl-4-hydroxy-5,6-difluoroquinoline. In 2 ml of dimethyl formamide was suspended 20 mg of 60% sodium hydride. The mixture (100 mg) of 2-ethyl-3-methyl-4-hydroxy-6,7-difluoroquinoline and 2-ethyl-3-methyl-4-hydroxy- 5,6-difluoroquinoline (starting material 1) was suspended in 2 ml of dimethyl formamide, and the suspension of the starting material 1 was added dropwise to the above suspension under ice cooling. The mixture was stirred for one hr, and 70 μl of cyclopropanecarbonyl chloride (starting material 2) was then added thereto. The mixture was stirred at room temperature for 3 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate, and the solvent was then removed by evaporation under the reduced pressure. The crude product thus obtained was purified on Wako Gel C-200 (100 ml; elution solvent=n-hexane-ethyl acetate (10:1)) to give 78.8 mg of 2-ethyl-3-methyl-4-cyclopropanecarbonyloxy-6,7-difluoroquinoline (compound 1) and 17.8 mg of 2-ethyl-3-methyl-4-cyclopropanecarbonyloxy-5,6-difluoroquinoline (compound 2). $^1$H-NMR data are shown in Table 3.

Alternative to Example 1

Synthesis of Starting Material 1 (Mixture of 2-ethyl-3-methyl-4-hydroxy-6,7-difluoroquinoline with 2-ethyl-3-methyl-4-hydroxy-5,6-difluoroquinoline)

3,4-Difluoroaniline (1.0 g) and 1.12 g of methyl-2-methylpropionyl acetate were stirred in 5 ml of xylene in the presence of 0.3 ml of boron trifluoride etherate at 140° C. for 3 hr. The reaction solution was allowed to stand for cooling, and the precipitate was then collected by filtration to give 603.7 mg of a mixture of 2-ethyl-3-methyl-4-hydroxy-6,7-difluoroquinoline with 2-ethyl-3-methyl-4-hydroxy-5,6-difluoroquinoline.

Example 2

2-Ethyl-3-methyl-4-acetyloxy-6,7-difluoroquinoline (compound 3)

2-Ethyl-3-methyl-4-cyclopropanecarbonyloxy-6,7-difluoroquinoline (5.5 g) prepared as described in Example 1 was dissolved in 50 ml of methanol. A solution of 2.5 g of sodium hydroxide in 50 ml of water was added to this solution, and the mixture was stirred at 50° C. for 3 hr. The reaction solution was allowed to stand for cooling and was then poured into 50 ml of water. The mixture was neutralized with 1N hydrochloric acid, and the precipitate was then collected by filtration to give 5.1 g of 2-ethyl-3-methyl-4-hydroxy-6,7-difluoroquinoline. In 20 ml of tetrahydrofuran was suspended 96 mg of 60% sodium hydride. Separately, 446 mg of the 2-ethyl-3-methyl-4-hydroxy-6,7-difluoroquinoline (starting material 1) was suspended in 10 ml of tetrahydrofuran, and this suspension of starting material 1 was added dropwise to the above suspension under ice cooling. The mixture was stirred for 1 hr, and 188.4 mg of acetyl chloride (starting material 2) was then added thereto. The mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate, and the solvent was then removed by evaporation under the reduced pressure. The crude product thus obtained was purified on Wako Gel C-200 (100 ml; elution solvent=n-hexane-ethyl acetate (10:1)) to give 168.6 mg of 2-ethyl-3-methyl-4-acetyloxy-6,7-difluoroquinoline (compound 3). $^1$H-NMR data are shown in Table 3.

Example 3

2-Ethyl-3-methyl-4-acetyloxy-5,6-difluoroquinoline (compound 12)

2-Ethyl-3-methyl-4-cyclopropanecarbonyloxy-5,6-difluoroquinoline (1 g) prepared as described in Example 1 was dissolved in 10 ml of methanol to prepare a solution. A solution of 0.5 g of sodium hydroxide in 10 ml of water was added to this solution, and the mixture was stirred at 50° C. for 3 hr. The reaction solution was allowed to stand for cooling and was then poured into 50 ml of water, and the mixture was neutralized with 1 N hydrochloric acid. The precipitate was then collected by filtration to give 700 mg of 2-ethyl-3-methyl-4-hydroxy-5,6-difluoroquinoline. In 20 ml of tetrahydrofuran was suspended in 96 mg of 60% sodium hydride. The 2-ethyl-3-methyl-4-hydroxy-5,6-difluoroquinoline (starting material 1) (446 mg) was suspended in 10 ml of tetrahydrofuran, and this suspension of starting material 1 was added dropwise to the above suspension under ice cooling. The mixture was stirred for one hr, 200 mg of acetyl chloride (starting material 2) was then added thereto, and the mixture was stirred at room temperature for 4.5 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 424 mg of 2-ethyl-3-methyl-4-acetyloxy-5,6-difluoroquinoline (compound 12). $^1$H-NMR data are shown in Table 3.

Example 4

2,3-Dimethyl-4-cyclopropanecarbonyloxy-6,7-difluoroquinoline (compound 15) and 2,3-dimethyl-4-cyclopropanecarbonyloxy-5,6-difluoroquinoline (compound 16)

3,4-Difluoroaniline (5.16 g) and 5.76 g of ethyl-2-methyl acetoacetate were refluxed in toluene (80 ml) in the presence of 0.3 ml of boron trifluoride etherate for 3 hr. The reaction mixture was washed with a saturated sodium hydrogencarbonate solution and saturated brine and was dried over anhydrous sodium sulfate, and the solvent was then removed by evaporation. The resultant intermediate was refluxed in diphenyl ether for 30 min. The reaction solution was allowed to stand for cooling, and the precipitate was then collected by filtration under the reduced pressure to give 4.0 g of a mixture of 2,3-dimethyl-4-hydroxy-6,7-difluoroquinoline with 2,3-dimethyl-4-hydroxy-5,6-difluoroquinoline. In 10 ml of tetrahydrofuran was suspended 230 mg of 60% sodium hydride. The mixture of 2,3-dimethyl-4-hydroxy-6,7-difluoroquinoline with 2,3-dimethyl-4-hydroxy-5,6-difluoroquinoline (starting material 1) (1 g) was suspended in 20 ml of tetrahydrofuran, and this suspension of starting material 1 was added dropwise to the above suspension under ice cooling. The reaction mixture was stirred for one hr. Cyclopropanecarbonyl chloride (starting material 2) (600 mg) was then added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (200 ml; elution solvent=n-hexane-ethyl acetate (10:1)) to give 890 mg of 2,3-dimethyl-4-cyclopropanecarbonyloxy-6,7-difluoroquinoline (compound 15) and 90.6 mg of 2,3-dimethyl-4-cyclopropanecarbonyloxy-5,6-difluoroquinoline (compound 16). $^1$H-NMR data are shown in Table 3.

Alternative to Example 4

Synthesis of Starting Material 1 (Mixture of 2,3-dimethyl-4-hydroxy-6,7-difluoroquinoline with 2,3-dimethyl-4-hydroxy-5,6-difluoroquinoline)

3,4-Difluoroaniline (1.0 g) and 1.11 g of methyl-2-methyl acetoacetate were stirred in 5 ml of xylene in the presence of 0.3 ml of boron trifluoride etherate at 140° C. for 3 hr. The reaction solution was allowed to stand for cooling, and the precipitate was then collected by filtration to give 906.8 mg of a mixture of 2,3-dimethyl-4-hydroxy-6,7-difluoroquinoline with 2,3-dimethyl-4-hydroxy-5,6-difluoroquinoline.

Example 5

2,3-Dimethyl-4-acetyloxy-6,7-difluoroquinoline (compound 17)

In 10 ml of tetrahydrofuran was suspended 230 mg of 60% sodium hydride. The mixture (1 g) of 2,3-dimethyl-4-hydroxy-6,7-difluoroquinoline with 2,3-dimethyl-4-hydroxy-5,6-difluoroquinoline (starting material 1) prepared as described in Example 4 was suspended in 20 ml of tetrahydrofuran, and this suspension of starting material 1 was added dropwise to the above suspension under ice cooling. The reaction mixture was stirred for one hr. Acetyl chloride (starting material 2) (450 mg) was added thereto, and the mixture was then stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (200 ml; elution solvent=n-hexane-ethyl acetate (10:1)) to give 262.5 mg of 2,3-dimethyl-4-acetyloxy-6,7-difluoroquinoline (compound 17). $^1$H-NMR data are shown in Table 3.

Example 6

2-Ethyl-3-methyl-4-acetyloxy-6-fluoro-7-chloroquinoline (compound 18) and 2-ethyl-3-methyl-4-acetyloxy-5-chloro-6-fluoroquinoline (compound 19)

3-Chloro-4-fluoroaniline (2.91 g) and 3.16 g of ethyl-2-methylpropionyl acetate were refluxed in toluene (60 ml) in the presence of 0.3 ml of boron trifluoride etherate for 3 hr. The reaction mixture was then washed with a saturated sodium hydrogencarbonate solution and saturated brine and was dried over anhydrous sodium sulfate, and the solvent was then removed by evaporation. The resultant intermediate was refluxed in diphenyl ether for 30 min. The reaction solution was allowed to stand for cooling, and the precipitate was then collected by filtration under the reduced pressure to give 820 mg of a mixture of 2-ethyl-3-methyl-4-hydroxy-6-fluoro-7-chloroquinoline with 2-ethyl-3-methyl-4-hydroxy-5-chloro-6-fluoroquinoline. In 10 ml of tetrahydrofuran was suspended 90.3 mg of 60% sodium hydride. The mixture of 2-ethyl-3-methyl-4-hydroxy-6-fluoro-7-chloroquinoline with 2-ethyl-3-methyl-4-hydroxy-5-chloro-6-fluoroquinoline (starting material 1) (400 mg) was suspended in 10 ml of tetrahydrofuran, and this suspension was added dropwise to the above suspension under ice cooling. The mixture was stirred for one hr. Acetyl chloride (starting material 2) (180 µl) was then added thereto, and the mixture was stirred at room temperature for 3 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 17.5 mg of 2-ethyl-3-methyl-4-acetyloxy-6-fluoro-7-chloroquinoline (compound 18) and 44.6 mg of 2-ethyl-3-methyl-4-acetyloxy-5-chloro-6-fluoroquinoline (compound 19). $^1$H-NMR data are shown in Table 3.

Example 7

2-Ethyl-3-methyl-4-cyclopropanecarbonyloxy-6-fluoro-7-chloroquinoline (compound 20) and 2-ethyl-3-methyl-4-cyclopropanecarbonyloxy-5-chloro-6-fluoro-quinoline (compound 21)

In 5 ml of tetrahydrofuran was suspended 90.3 mg of 60% sodium hydride. Separately, 400 mg of the mixture of 2-ethyl-3-methyl-4-hydroxy-6-fluoro-7-chloroquinoline with 2-ethyl-3-methyl-4-hydroxy-5-chloro-6-fluoroquinoline (starting material 1) prepared as described in Example 6 was suspended in 10 ml of tetrahydrofuran, and this suspension was added dropwise to the above suspension under ice cooling. The mixture was stirred for one hr. Cyclopropanecarbonyl chloride (starting material 2) (240 mg) was then added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate, and the solvent was then removed by evaporation under the reduced pressure. The crude product thus obtained was purified on Wako Gel C-200 (200 ml; elution solvent=n-hexane-ethyl acetate (10:1)) to give 245.4 mg of 2-ethyl-3-methyl-4-cyclopropanecarbonyloxy-6-fluoro-7-chloroquinoline (compound 20) and 129.2 mg of 2-ethyl-3-methyl-4-cyclopropanecarbonyloxy-5-chloro-6-fluoroquinoline (compound 21). $^1$H-NMR data are shown in Table 3.

Example 8

2-Ethyl-3-methyl-4-isopropoxycarbonyloxy-6-fluoro-7-chloroquinoline (compound 22) 2-ethyl-3-methyl-4-isopropoxycarbonyloxy-5-chloro-6-fluoroquinoline (compound 23)

In ml of tetrahydrofuran was suspended 96 mg of 60% sodium hydride. The mixture of 2-ethyl-3-methyl-4-hydroxy-6-fluoro-7-chloroquinoline with 2-ethyl-3-methyl-4-hydroxy-5-chloro-6-fluoroquinoline (starting material 1) (480 mg) prepared as described in Example 6 was suspended in 10 ml of tetrahydrofuran, and this suspension was added dropwise to the above suspension under ice cooling. After stirring for one hr, 300 mg of isopropyl chloroformate (starting material 2) was added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (200 ml; elution solvent=n-hexane-ethyl acetate (10:1)) to give 345.1 mg of 2-ethyl-3-methyl-4-isopropoxycarbonyloxy-6-fluoro-7-chloroquinoline (compound 22) and 170.7 mg of 2-ethyl-3-methyl-4-isopropoxycarbonyloxy-5-chloro-6-fluoro -quinoline (compound 23). $^1$H-NMR data are shown in Table 3.

Example 9

2,3-Dimethyl-4-cyclopropanecarbonyloxy-6-fluoro-7-chloroquinoline (compound 26) and 2,3-dimethyl-4-cyclopropanecarbonyloxy-5-chloro-6-fluoroquinoline (compound 27)

3-Chloro-4-fluoroaniline (5.0 g) and 4.9 g of ethyl-2-methyl acetoacetate were refluxed in toluene (50 ml) in the presence of 0.3 ml of boron trifluoride etherate for 3 hr. The reaction mixture was washed with a saturated sodium hydrogencarbonate solution and saturated brine and was dried over anhydrous sodium sulfate, and the solvent was then removed by evaporation. The resultant intermediate was refluxed in diphenyl ether for 30 min. The reaction mixture was allowed to stand for cooling, and the precipitate was then collected by filtration under the reduced pressure to give 1.7 g of a mixture of 2,3-dimethyl-4-hydroxy-6-fluoro-7-chloroquinoline with 2,3-dimethyl-4-hydroxy-5-chloro-6-fluoroquinoline. In 50 ml of dimethyl formamide was suspended 350 mg of 60% sodium hydride. Separately, the mixture of 2,3-dimethyl-4-hydroxy-6-fluoro-7-chloroquinoline with 2,3-dimethyl-4-hydroxy-5-chloro-6-fluoroquinoline (starting material 1) (1.7 g) was suspended in 30 ml of dimethyl formamide, and this suspension was added dropwise to the above suspension under ice cooling. After stirring for one hr, 940 μl of cyclopropanecarbonyl chloride (starting material 2) was added thereto, and the mixture was stirred at room temperature for 13 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 480 mg of 2,3-dimethyl-4-cyclopropanecarbonyloxy-6-fluoro-7-chloroquinoline (compound 26) and 350 mg of 2,3-dimethyl-4-cyclopropanecarbonyloxy-5-chloro-6-fluoro -quinoline (compound 27). $^1$H-NMR data are shown in Table 3.

Example 10

2,3-Dimethyl-4-methoxycarbonyloxy-6-fluoro-7-chloroquinoline (compound 28)

2,3-Dimethyl-4-cyclopropanecarbonyloxy-6-fluoro-7-chloroquinoline (590 mg) prepared as described in Example 9 was dissolved in 5 ml of methanol, and 5 ml of a 10% aqueous sodium hydroxide solution was added to this solution. The mixture was stirred at 50° C. for 3 hr. The reaction mixture was allowed to stand for cooling, was then poured into 50 ml of water, and was neutralized with 1 N hydrochloric acid, and the precipitate was then collected by filtration to give 400 mg of 2,3-dimethyl-4-hydroxy-6-fluoro-7-chloroquinoline. In 3 ml of tetrahydrofuran was suspended 26.4 mg of 60% sodium hydride. Separately, 100 mg of 2,3-dimethyl-4-hydroxy-6-fluoro-7-chloroquinoline (starting material 1) prepared above was suspended in 2 ml of tetrahydrofuran, and this suspension was added dropwise to the above suspension under ice cooling. After stirring for one hr, 0.1 ml of methyl chloroformate (starting material 2) was added thereto, and the mixture was stirred at room temperature for 3 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 48 mg of 2,3-dimethyl-4-methoxycarbonyloxy-6-fluoro-7-chloroquinoline (compound 28). $^1$H-NMR data are shown in Table 3.

Example 11

2-Ethyl-3-methyl-4-methoxycarbonyloxy-5-chloro-6-fluoroquinoline (compound 36)

2-Ethyl-3-methyl-4-cyclopropanecarbonyloxy-5-chloro-6-fluoroquinoline (1.5 g) prepared as described in Example 7 was dissolved in 70 ml of methanol. To this solution was added 30 ml of a 10% aqueous sodium hydroxide solution. The mixture was stirred at 50° C. for 1.5 hr. The reaction mixture was allowed to stand for cooling, was then poured into 50 ml of water, and was neutralized with 1 N hydrochloric acid, and the precipitate was then collected by filtration to give 1.17 g of 0.2-ethyl-3-methyl-4-hydroxy-5-chloro-6-fluoroquinoline. In 15 ml of dimethyl formamide was suspended 40.1 mg of 60% sodium hydride. Separately, 200 mg of 2-ethyl-3-methyl-4-hydroxy-5-chloro-6-fluoroquinoline (starting material 1) prepared above was suspended in 2 ml of dimethyl formamide, and this suspension was added dropwise to the above suspension under ice cooling. After stirring for one hr, 78.5 mg of methyl chloroformate (starting material 2) was added thereto, and the mixture was stirred at room temperature for 3 hr. The reaction solution was poured into water, and the mixture was extracted with ethyl acetate. The ethyl acetate layer was washed with a saturated aqueous sodium hydrogencarbonate solution and saturated, brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 218.8 mg of 2-ethyl-3-methyl-4-methoxycarbonyloxy-5-chloro-6-fluoroquinoline (compound 36). $^1$H-NMR data are shown in Table 3.

Example 12

2,3-Dimethyl-4-acetoxy-5,6-difluoroquinoline (compound 44)

2,3-Dimethyl-4-cyclopropanecarbonyloxy-5,6-difluoroquinoline (1.5 g) prepared as described in Example 4 was dissolved in 15 ml of methanol. A 10% aqueous sodium hydroxide solution (15 ml) was added to the solution, and the mixture was stirred at 50° C. for 1.5 hr. The reaction mixture was allowed to stand for cooling, was then poured into 50 ml of water, and was neutralized with 1 N hydrochloric acid, and the precipitate was then collected by filtration to give 1.1 g of 2,3-dimethyl-4-hydroxy-5,6-difluoroquinoline. In 5 ml of dimethyl formamide was suspended 11.5 mg of 60% sodium hydride. Separately, 50 mg of 2,3-dimethyl-4-hydroxy-5,6-difluoroquinoline (starting material 1) prepared above was suspended in 5 ml of dimethyl formamide, and this suspension was added dropwise to the above suspension under ice cooling. After stirring for one hr, 20 mg of acetyl chloride (starting material 2) was added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 54.2 mg of 2,3-dimethyl-4-acetoxy-5,6-difluoroquinoline (compound 44). $^1$H-NMR data are shown in Table 3.

Example 13

2,3-Dimethyl-4-(3-transchloroacryloyloxy)- 5,6-difluoroquinoline (compound 53) and 2,3-dimethyl-4-(3-cischloroacryloyloxy)-5,6-difluoroquinoline (compound 54)

Thionyl chloride (300 μl) was added to 213 mg of 3-cischloroacrylic acid, and the mixture was stirred at 60° C. for one hr. Thionyl chloride was removed by evaporation under the reduced pressure to give 3-chloroacrylic acid chloride.

In 5 ml of dimethyl formamide was suspended 11.5 mg of 60% sodium hydride. Separately, 50 mg of 2,3-dimethyl-4-hydroxy-5,6-difluoroquinoline (starting material 1) prepared as described in Example 12 was suspended in 5 ml of dimethyl formamide, and this suspension was added dropwise to the above suspension under ice cooling. After stirring for one hr, 50 mg of 3-chloroacrylic acid chloride (starting material 2) was added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 13.6 mg of 2,3-dimethyl-4-(3-transchloroacryloyloxy)-5,6-difluoroquinoline (compound 53) and 10.3 mg of 2,3-dimethyl-4-(3-cischloroacryloyloxy)-5,6-difluoro -quinoline (compound 54). $^1$H-NMR data are shown in Table 3.

Example 14

2,3-Dimethyl-4-cyclopropanecarbonyloxy-5-trifluoromethyl-6-fluoroquinoline (compound 61) and 2,3-dimethyl-4-cyclopropanecarbonyloxy-6-fluoro-7-trifluoro -methylquinoline (compound 63)

4-Fluoro-3-trifluoromethylaniline (1.0 g) and 0.81 g of methyl-2-methyl acetoacetate were stirred in xylene in the presence of 0.3 ml of boron trifluoride etherate at 140° C. for 3 hr. The reaction solution was allowed to stand for cooling, and the precipitate was then collected by filtration to give 228.2 mg of a mixture of 2,3-dimethyl-4-hydroxy-5-trifluoromethyl-6-fluoro-quinoline with 2,3-dimethyl-4-hydroxy-6-fluoro-7-trifluoromethylquinoline.

In 3 ml dimethyl formamide was suspended 18.8 mg of 60% sodium hydride. The mixture of 2,3-dimethyl-4-hydroxy-5-trifluoromethyl-6-fluoroquinoline with 2,3-dimethyl-4-hydroxy-6-fluoro-7-trifluoromethylquinoline (starting material 1) (100 mg) was suspended in 3 ml of dimethyl formamide, and this suspension was added dropwise to the above suspension under ice cooling. After stirring for one hr, 40.8 mg of cyclopropanecarbonyl chloride (starting material 2) was added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on a silica gel packed column (Varian) (20 g; elution solvent=n-hexane-ethyl acetate (40:1) to (20:1)) to give 27.9 mg of 2,3-dimethyl-4-cyclopropanecarbonyloxy-5-trifluoromethyl-6-fluoroquinoline (compound 61) and 51.3 mg of 2,3-dimethyl-4-cyclopropanecarbonyloxy-6-fluoro-7-trifluoro -methylquinoline (compound 63). $^1$H-NMR data are shown in Table 3.

Example 15

2,3-Dimethyl-4-cyclopropanecarbonyloxy-5,6-dichloroquinoline (compound 66) and 2,3-dimethyl-4-cyclopropanecarbonyloxy-6, 7-dichloroquinoline (compound 69)

3,4-Dichloroaniline (1.0 g) and 0.89 g of methyl- 2-methyl acetoacetate were stirred in xylene in the presence of 0.3 ml of boron trifluoride etherate at 140° C. for 3 hr. The reaction solution was allowed to stand for cooling, and the precipitate was then collected by filtration to give 667.4 mg of a mixture of 2,3-dimethyl-4-hydroxy-5,6-dichloroquinoline with 2,3-dimethyl-4-hydroxy-6,7-dichloroquinoline.

In 3 ml of dimethyl formamide was suspended 40.0 mg of 60% sodium hydride. Separately, the mixture of 2,3-dimethyl-4-hydroxy-5,6-dichloroquinoline with 2,3-dimethyl-4-hydroxy-6,7-dichloroquinoline (starting material 1) (200 mg) was suspended in 3 ml of dimethyl formamide, and this suspension was added dropwise to the above suspension under ice cooling. After stirring for one hr, 86.7 mg of cyclopropanecarbonyl chloride (starting material 2) was added thereto, and the mixture was stirred at room temperature for 15 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10: 1)) to give 75.2 mg of 2,3-dimethyl-4-cyclopropanecarbonyloxy-5,6-dichloroquinoline (compound 66) with 4 mg of 2,3-dimethyl-4-cyclopropanecarbonyloxy-6, 7-dichloroquinoline (compound 69). $^1$H-NMR data are shown in Table 3.

Example 16

2,3-Dimethyl-4-(5-hexynoylcarbonyloxy)-5,6-difluoroquinoline (compound 58)

5-Hexynoic acid (starting material 2) (26.9 mg), 40.6 mg of 2-chloro-1,3-dimethylimidazolinium chloride and 37.9 mg of pyridine were stirred in dichloromethane (5 ml) at room temperature for one hr. Thereafter, 50 mg of 2,3-dimethyl-4-hydroxy-5,6-difluoroquinoline (starting material 1) prepared as described in Example 12 was added thereto, and the mixture was stirred at room temperature for 15 hr. Water was added to the reaction solution, and the mixture was extracted with dichloromethane. The dichloromethane layer was washed with a saturated aqueous sodium hydrogencarbonate solution and was then dried over anhydrous sodium sulfate. The solvent was then removed by evaporation under the reduced pressure. The crude product thus obtained was purified on Wako Gel C-200 (10 ml; elution solvent=n-hexane-ethyl acetate (10:1)) to give 77.8 mg of 2,3-dimethyl-4-(5-hexynoylcarbonyloxy)-5,6-difluoroquinoline (compound 58). $^1$H-NMR data are shown in Table 3.

Example 17

2-Ethyl-3-methyl-4-methanethiolcarbonyloxy-5,6-difluoroquinoline (compound 39)

2-Ethyl-3-methyl-4-hydroxy-5,6-difluoroquinoline (starting material 1) (30 mg) prepared as described in Example 3 was suspended in dichloromethane under an argon atmosphere in the presence of dimethylaminopyridine. Triethylamine (16 mg) was added thereto, and the mixture was stirred at room temperature for 30 min. Thereafter, 16 mg of methyl chlorothioformate (starting material 2) was added thereto, and the mixture was stirred overnight. The reaction solution as such was concentrated, and the residue was then purified on Wako Gel C-200 (10 ml; elution solvent=n-hexane-ethyl acetate (10:1)) to give 40 mg of 2-ethyl-3-methyl-4-methanethiolcarbonyloxy-5,6-difluoroquinoline (compound 39). $^1$H-NMR data are shown in Table 3.

Example 18

2-Isopropyl-3-methyl-4-cyclopropanecarbonyl-oxy-6,7-difluoroquinoline (compound 34)

3,4-Difluoroaniline (4.5 g) and 6 g of ethyl-2-methyl isovalerylacetate were refluxed in toluene (50 ml) in the presence of 0.3 ml of boron trifluoride etherate for 3 hr. The reaction mixture was washed with a saturated sodium hydrogencarbonate solution and saturated brine and was dried over anhydrous sodium sulfate, and the solvent was then removed by evaporation. The resultant intermediate was refluxed in diphenyl ether for 30 min. The reaction mixture was allowed to stand for cooling, and the precipitate was then collected by filtration under the reduced pressure to give 246 mg of a mixture of 2-isopropyl-3-methyl-4-hydroxy-6,7-difluoroquinoline with 2-isopropyl-3-methyl-4-hydroxy-5,6-difluoroquinoline. In 10 ml of dimethyl formamide was suspended 20 mg of 60% sodium hydride. Separately, 100 mg of the mixture of 2-isopropyl-3-methyl-4-hydroxy-6,7-difluoroquinoline with 2-isopropyl-3-methyl-4-hydroxy-5,6-difluoroquinoline (starting material 1) was suspended in 20 ml of dimethyl formamide, and this suspension was added dropwise to the above suspension under ice cooling. After stirring for one hr, 100 mg of cyclopropanecarbonyl chloride (starting material 2) was added thereto, and the mixture was stirred at room temperature for 3 hr. The reaction solution was poured into water, and the mixture was extracted with ethyl acetate. The ethyl acetate layer was washed with a saturated aqueous sodium hydrogencarbonate solution and saturated brine and was then dried over anhydrous sodium sulfate. The solvent was then removed by evaporation under the reduced pressure. The crude product thus obtained was purified on Wako Gel C-200 (100 ml; elution solvent=n-hexane-ethyl acetate (10:1)) to give 44.1 mg of 2-isopropyl-3-methyl-4-cyclopropanecarbonyloxy-6,7-difluoroquinoline (compound 34). $^1$H-NMR data are shown in Table 3.

Chemical structures in formula (I) of compounds 1 to 3, 12, 15 to 23, 26 to 28, 34, 36, 39, 44, 53, 54, 58, 61, 63, 66, and 69 synthesized in Examples 1 to 18 were as follows.

TABLE 1

| Compd. No. | Name of compound | $R^1$ | $R^2$ | $R^3$ | $R^4$ | X |
|---|---|---|---|---|---|---|
| 1 | 2-ethyl-3-methyl-4-cyclopropanecarbonyloxy-6,7-difluoroquinoline | c-Pr | Et | H | F | F |
| 2 | 2-ethyl-3-methyl-4-cyclopropanecarbonyloxy-5,6-difluoroquinoline | c-Pr | Et | F | H | F |
| 3 | 2-ethyl-3-methyl-4-acetyloxy-6,7-difluoroquinoline | Me | Et | H | F | F |
| 12 | 2-ethyl-3-methyl-4-acetyloxy-5,6-difluoroquinoline | Me | Et | F | H | F |
| 15 | 2,3-dimethyl-4-cyclopropanecarbonyloxy-6,7-difluoroquinoline | c-Pr | Me | H | F | F |
| 16 | 2,3-dimethyl-4-cyclopropanecarbonyloxy-5,6-difluoroquinoline | c-Pr | Me | F | H | F |
| 17 | 2,3-dimethyl-4-acetyloxy-6,7-difluoro-quinoline | Me | Me | H | F | F |
| 18 | 2-ethyl-3-methyl-4-acetyloxy-6-fluoro-7-chloroquinoline | Me | Et | H | Cl | F |
| 19 | 2-ethyl-3-methyl-4-acetyloxy-5-chloro-6-fluoroquinoline | Me | Et | Cl | H | F |
| 20 | 2-ethyl-3-methyl-4-cyclopropanecarbonyloxy-6-fluoro-7-chloroquinoline | c-Pr | Et | H | Cl | F |
| 21 | 2-ethyl-3-methyl-4-cyclopropanecarbonyloxy-5-chloro-6-fluoroquinoline | c-Pr | Et | Cl | H | F |
| 22 | 2-ethyl-3-methyl-4-isopropoxycarbonyloxy-6-fluoro-7-chloroquinoline | O-i-Pr | Et | H | Cl | F |
| 23 | 2-ethyl-3-methyl-4-isopropoxycarbonyloxy-5-chloro-6-fluoroquinoline | O-i-Pr | Et | Cl | H | F |
| 26 | 2,3-dimethyl-4-cyclopropanecarbonyloxy-6-fluoro-7-chloroquinoline | c-Pr | Me | H | Cl | F |
| 27 | 2,3-dimethyl-4-cyclopropanecarbonyloxy-5-chloro-6-fluoroquinoline | c-Pr | Me | Cl | H | F |

TABLE 1-continued

| Compd. No. | Name of compound | $R^1$ | $R^2$ | $R^3$ | $R^4$ | X |
|---|---|---|---|---|---|---|
| 28 | 2,3-dimethyl-4-methoxycarbonyloxy-6-fluoro-7-chloroquinoline | O-Me | Me | H | Cl | F |
| 34 | 2-isopropyl-3-methyl-4-cyclopropane-carbonyloxy-6,7-difluoroquinoline | c-Pr | i-Pr | H | F | F |
| 36 | 2-ethyl-3-methyl-4-methoxycarbonyloxy-5-chloro-6-fluoroquinoline | O-Me | Et | Cl | H | F |
| 39 | 2-ethyl-3-methyl-4-methanethiolcarbonyloxy-5,6-difluoroquinoline | S-Me | Et | F | H | F |
| 44 | 2,3-dimethyl-4-acetoxy-5,6-difluoro-quinoline | Me | Me | F | H | F |
| 53 | 2,3-dimethyl-4-(3-transchloroacryloyloxy)-5,6-difluoroquinoline | trans-CH=CH-Cl | Me | F | H | F |
| 54 | 2,3-dimethyl-4-(3-cischloroacryloyloxy)-5,6-difluoroquinoline | cis-CH=CH-Cl | Me | F | H | F |
| 58 | 2,3-dimethyl-4-(5-hexynoyloxy)-5,6-difluoroquinoline | 4-Pentynyl | Me | F | H | F |
| 61 | 2,3-dimethyl-4-cyclopropanecarbonyloxy-5-trifluoromethyl-6-fluoroquinoline | c-Pr | Me | $CF_3$ | H | F |
| 63 | 2,3-dimethyl-4-cyclopropanecarbonyloxy-6-fluoro-7-trifluoromethylquinoline | c-Pr | Me | H | $CF_3$ | F |
| 65 | 2,3-dimethyl-4-acetoxy-5,6-dichloro-quinoline | Me | Me | Cl | H | Cl |
| 66 | 2,3-dimethyl-4-cyclopropanecarbonyloxy-5,6-dichloroquinoline | c-Pr | Me | Cl | H | Cl |
| 68 | 2,3-dimethyl-4-acetoxy-6,7-dichloro-quinoline | Me | Me | H | Cl | Cl |
| 69 | 2,3-dimethyl-4-cyclopropanecarbonyloxy-6,7-dichloroquinoline | c-Pr | Me | H | Cl | Cl |

Compounds 4 to 11, 13, 14, 24, 25, 29 to 33, 35, 37, 38, 40 to 43, 45 to 52, 55 to 57, 59, 60, 62, 64, 67, and 70 to 81 were synthesized as described in the above examples. The name of compounds, starting materials, yields, and chemical structures in formula (I) were as follows.

TABLE 2

| Compd. No. | Name of compound | $R^1$ | $R^2$ | $R^3$ | $R^4$ | X |
|---|---|---|---|---|---|---|
| 4 | 2-ethyl-3-methyl-4-propionyloxy-6,7-difluoroquinoline | Et | Et | H | F | F |
| 5 | 2-ethy-3-methyl-4-valeryloxy-6,7-difluoroquinoline | n-$C_4H_9$ | Et | H | F | F |
| 6 | 2-ethyl-3-methyl-4-cyclobutanecarbonyloxy-6,7-difluoroquinoline | c-Bu | Et | H | F | F |
| 7 | 2-ethyl-3-methyl-4-isovaleryloxy-6,7-difluoroquinoline | i-Bu | Et | H | F | F |
| 8 | 2-ethyl-3-methyl-4-methoxycarbonyloxy-6,7-difluoroquinoline | O—Me | Et | H | F | F |
| 9 | 2-ethyl-3-methyl-4-ethoxycabonyloxy-6,7-difluoroquinoline | O—Et | Et | H | F | F |
| 10 | 2-ethyl-3-methyl-4-butoxycarbonyloxy-6,7-difluoroquinoline | O-n-Bu | Et | H | F | F |
| 11 | 2-ethyl-3-methyl-4-isopropoxycarbonyloxy-6,7-difluoroquinoline | O-i-Pr | Et | H | F | F |
| 13 | 2-ethyl-3-methyl-4-butoxycarbonyloxy-5,6-difluoroquinoline | O-n-Bu | Et | F | H | F |
| 14 | 2-ethyl-3-methyl-4-isopropoxycarbonyloxy-5,6-difluoroquinoline | O-i-Pr | Et | F | H | F |
| 24 | 2-ethyl-3-methyl-4-methoxycarbonyloxy-5,6-difluoroquinoline | O—Me | Et | F | H | F |
| 25 | 2,3-dimethyl-4-methoxycarbonyl-oxy-5,6-difluoroquinoline | O—Me | Me | F | H | F |
| 29 | 2,3-dimethyl-4-acetoxy-6-fluoro-7-chloroquinoline | Me | Me | H | Cl | F |
| 30 | 2-ethyl-3-methyl-4-propionyloxy-5,6-difluoroqinoline | Et | Et | F | H | F |
| 31 | 2-ethyl-3-methyl-4-cyclobutanecarboxyloxy-5,6-difluoroquinoline | c-Bu | Et | F | H | F |
| 32 | 2-ethyl-3-methyl-4-isobutanecarboxyloxy-5,6-difluoroquinaline | i-Bu | Et | F | H | F |
| 33 | 2-ethyl-3-methyl-4-ethoxycarbonyl-oxy-5,6-difluoroquinoline | O—Et | Et | F | H | F |

TABLE 2-continued

| | | | | | | |
|---|---|---|---|---|---|---|
| 35 | 2-isopropyl-3-methyl-4-methoxycarbonyloxy-6,7-difluoroquinoline | O—Me | i-Pr | H | F | F |
| 37 | 2-ethyl-3-methyl-4-butoxycarbonyloxy-5-chloro-6-fluoroquinoline | O-n-Bu | Et | Cl | H | F |
| 38 | 2-ethyl-3-methyl-4-ethoxycarbonyloxy-5-chloro-6-fluoroquinoline | O—Et | Et | Cl | H | F |
| 40 | 2-ethyl-3-methyl-4-vinyloxycarbonyloxy-5,6-difluoroquinoline | O-Vinyl | Et | F | H | F |
| 41 | 2-ethyl-3-methyl-4-propargyloxycarbonyloxy-5,6-difluoroquinoline | O-Propargyl | Et | F | H | F |
| 42 | 2-ethyl-3-methyl-4-chloromethyloycarbonyloxy-5,6-difluoroquinoline | O—CH$_2$Cl | Et | F | H | F |
| 43 | 2-ethyl-3-methyl-4-chloroacetyloxy-5,6-difluoroquinoline | CH$_2$Cl | Et | F | H | F |
| 45 | 2,3-dimethyl-4-ethyloxycarbonyloxy-5,6-difluoroquinoline | O—Et | Me | F | H | F |
| 46 | 2,3-dimethyl-4-methanethiolcarbonyloxy-5,6-difluoroquinoline | S—Me | Me | F | H | F |
| 47 | 2-ethyl-3-methyl-4-acryloxyloxy-5,6-difluoroquinoline | Vinyl | Et | F | H | F |
| 48 | 2-ethyl-3-methyl-4-isobutyryloxy-5,6-difluoroquinoline | i-Bu | Et | F | H | F |
| 49 | 2,3-dimethyl-4-(2-methyl-3,3-difluorocyclopropanecarbonyloxy)-5,6-difluoroquinoline | (2-methyl-3,3-difluorocyclopropyl) | Me | F | H | F |
| 50 | 2,3-dimethyl-4-propargloxycarbonyloxy-5,6-difluoroquinoline | O-Propargyl | Me | F | H | F |
| 51 | 2,3-dimethyl-4-vinyloxycarbonyloxy-5,6-difluoroquinoline | O-Vinly | Me | F | H | F |
| 52 | 2,3-dimethyl-4-(3-butynyl)oxycarbonyloxy-5,6-difluoroquinoline | O-(3-Butynyl) | Me | F | H | F |
| 55 | 2-ethyl-3-methyl-4-propanethiolcarbonyloxy-5,6-difluoroquinoline | S—Pr | Et | F | H | F |
| 56 | 2-ethyl-3-methyl-4-(3-butynyl)oxycarbonyloxy-5,6-difluoroquinoline | O-(3-Butynyl) | Et | F | H | F |
| 57 | 2,3-dimethyl-4-allyloxycarbonyloxy-5,6-difluoroquinoline | O-Allyl | Me | F | H | F |
| 59 | 2,3-dimethyl-4-(4-pentynoyl)oxy-5,8-difluoroquinoline | 3-Butynyl | Me | F | H | F |
| 60 | 2,3-dimethyl-4-(3,3,3-trifluoropropionyloxy)-5,6-difluoroquinoline | CH$_2$CF$_3$ | Me | F | H | F |
| 62 | 2,3-dimethyl-4-methoxycarbonyloxy-5-trifluoromethyl-6-fluoroquinoline | O—Me | Me | CF3 | H | F |
| 64 | 2,3-dimethyl-4-methoxycarbonyloxy-6-fluoro-7-trifluoromethyl-quinoline | O—Me | Me | H | CF3 | F |
| 66 | 2,3-dimethyl-4-cyclopropanecarbonyloxy-5,6-dichloroquinoline | c-Pr | Me | Cl | H | Cl |
| 67 | 2,3-dimethyl-4-methoxycarbonyloxy-5,6-dichloroquinoline | O—Me | Me | Cl | H | Cl |
| 69 | 2,3-dimethyl-4-cyclopropanecarbonyloxy-6,7-dichloroquinoline | c-Pr | Me | H | Cl | Cl |
| 70 | 2,3-dimethyl-4-methoxycarbonyloxy-6,7-dicloroquinoline | O—Me | Me | H | Cl | Cl |
| 71 | 2-ethyl-3-methyl-4-cyclopropylethyloxycarbonyloxy-5,6-difluoroquinoline | O-CH$_2$CH$_2$-cyclopropyl | Et | F | H | F |
| 72 | 2-ethyl-3-methyl-4-(3,3,3-trifluoropropyloxycarbonyloxy)-5,6-difluroquinoline | O-CH$_2$CH$_2$CF$_3$ | Et | F | H | F |
| 73 | 2-ethyl-3-methyl-4-(3-pentynyloxycabonyloxy-5,6-difluoroquinoline | O-CH$_2$CH$_2$C≡CCH$_3$ | Et | F | H | F |
| 74 | 2,3-dimethyl-4-cyclopropylethyloxycarbonyloxy-5,6-difluoroquinoline | O-CH$_2$CH$_2$-cyclopropyl | Me | F | H | F |
| 75 | 2,3-dimethyl-4-(3,3,3-trifluoropropyloxycarbonyloxy)-5,6-difluoroquinolane | O-CH$_2$CH$_2$CF$_3$ | Me | F | H | F |
| 76 | 2,3-dimethyl-4-(3-pentynyloxycarbonyloxy)-5,6-difluoroquinoline | O-CH$_2$CH$_2$C≡CCH$_3$ | Me | F | H | F |
| 77 | 2,3-dimethyl-4-cyclopropylethyloxycarbonyloxy-6,7-difluoroquinoline | O-CH$_2$CH$_2$-cyclopropyl | Me | H | F | F |

TABLE 2-continued

| # | Name | Structure | R1 | R2 | R3 | R4 |
|---|------|-----------|----|----|----|----|
| 78 | 2,3-dimethyl-4-(3,3,3-trifluoropropyloxycarbonyloxy)-6,7-difluoroquinoline | O−CH2CH2−CF3 | Me | H | F | F |
| 79 | 2,3-dimethyl-4-(3-pentynyloxycarbonyloxy)-6,7-difluoroquinoline | O−CH2CH2−C≡C−CH3 | Me | H | F | F |
| 80 | 2-ethyl-3-methyl-4-(2-cyanoethyloxycarbonyloxy)-5,6-difluoro-quinoline | O−CH2CH2−CN | Et | F | H | F |
| 81 | 2,3-dimethyl-4-2-cyanoethylocycarbonyloxy-5,6-difluoroquinoline | O−CH2CH2−CN | Me | F | H | F |

| Compd. No. | Production process (Ex. No.) | Starting material 1 | Starting material 2 | | Yield |
|---|---|---|---|---|---|
| 4 | 2 | 446 mg | propionyl chloride | 222 mg | 209.9 mg |
| 5 | 2 | 446 mg | valeryl chloride | 289.2 mg | 204.5 mg |
| 6 | 2 | 446 mg | cyclobutanecarbonyl chloride | 284.4 mg | 221.6 mg |
| 7 | 2 | 446 mg | isovaleryl chloride | 289.2 mg | 253.1 mg |
| 8 | 2 | 446 mg | methyl chloroformate | 226.8 mg | 429.4 mg |
| 9 | 2 | 446 mg | ethyl chloroformate | 260.4 mg | 518.4 mg |
| 10 | 2 | 446 mg | n-butyl chloroformate | 327.6 mg | 568.7 mg |
| 11 | 2 | 446 mg | isopropyl chloroformate | 294 mg | 452.3 mg |
| 13 | 3 | 250 mg | n-butyl chloroformate | 170 mg | 328.4 mg |
| 14 | 3 | 250 mg | isopropyl chloroformate | 200 mg | 363.2 mg |
| 24 | 3 | 112 mg | methyl chloroformate | 100 mg | 80 mg |
| 25 | 12 | 200 mg | methyl chloroformate | 150 mg | 228.9 mg |
| 29 | 10 | 100 mg | acetyl chloride | 100 mg | 34 mg |
| 30 | 3 | 200 mg | propionyl chloride | 100 mg | 202.7 mg |
| 31 | 3 | 200 mg | cyclobutanecarbonyl chloride | 128 mg | 231 mg |
| 32 | 3 | 200 mg | isobutanecarbonyl chloride | 128 mg | 234.8 mg |
| 33 | 3 | 200 mg | ethyl chloroformate | 117.2 mg | 222.9 mg |
| 35 | 18 | 50 mg | methyl chloroformate | 20 mg | 45.3 mg |
| 37 | 11 | 200 mg | butyl chloroformate | 120.5 mg | 235.7 mg |
| 38 | 11 | 200 mg | ethyl chloroformate | 108.5 mg | 244.0 mg |
| 40 | 17 | 30 mg | vinyl chloroformate | 16 mg | 25 mg |
| 41 | 17 | 30 mg | propargyl chloroformate | 17 mg | 9 mg |
| 42 | 17 | 30 mg | chloromethyl chloroformate | 18 mg | 4.8 mg |
| 43 | 17 | 30 mg | chloroacetyl chloride | 16 mg | 11.3 mg |
| 45 | 12 | 50 mg | ethyl chloroformate | 30 mg | 57.9 mg |
| 46 | 12 | 50 mg | methyl chlorothioformate | 30 mg | 33.1 mg |
| 47 | 17 | 30 mg | acryloyl chloride | 14 mg | 27.5 mg |
| 48 | 17 | 30 mg | isobutyryl chloride | 15 mg | 31.2 mg |
| 49 | 12 | 30 mg | 2-methyl-3,3-difluoro-cyclopropanecarbonyl chloride | 26 mg | 10.5 mg |
| 50 | 12 | 50 mg | propargyl chloroformate | 30 mg | 60 mg |
| 51 | 12 | 30 mg | vinyl chloroformate | 30 mg | 22.7 mg |
| 52 | 12 | 50 mg | 3-butynyl chloroformate | 50 mg | 32.7 mg |
| 55 | 3 | 30 mg | propyl chlorothioformate | 50 mg | 15.1 mg |
| 56 | 3 | 50 mg | 3-butynyl chloroformate | 50 mg | 58.4 mg |
| 57 | 12 | 50 mg | allyl chloroformate | 28.9 mg | 29.2 mg |
| 59 | 16 | 50 mg | 4-pentinic acid | 23.5 mg | 46.9 mg |
| 60 | 12 | 50 mg | 3,3,3-trifluoropropionic acid | 30.7 mg | 40.4 mg |
| 62 | 14 | 100 mg | methyl chloroformate | 36.9 mg | 40.6 mg |
| 64 | 14 | 100 mg | methyl chloroformate | 36.9 mg | 54.3 mg |
| 66 | 15 | 200 mg | cyclopropanecarbonyl chloride | 86.7 mg | 75.2 mg |
| 67 | 15 | 200 mg | methyl chloroformate | 78.4 mg | 110.1 mg |
| 69 | 15 | 200 mg | cyclopropanecarbonyl chloride | 86.7 mg | 4 mg |
| 70 | 15 | 200 mg | methyl chloroformate | 78.4 mg | 40.9 mg |
| 71 | 3 | 100 mg | cyclopropylethyl chloroformate | 80.2 mg | 133.6 mg |
| 72 | 3 | 100 mg | 3,3,3-trifluoropropyl chloroformate | 95.3 mg | 81.2 mg |
| 73 | 3 | 100 mg | 3-pentyl chloroformate | 79.2 mg | 137.6 mg |
| 74 | 4 | 200 mg | cyclopropylethyl chloroformate | 170.9 mg | 56.6 mg |
| 75 | 4 | 200 mg | 3,3,3-trifluoropropyl chloroformate | 203 mg | 37.3 mg |

TABLE 2-continued

| | | | | | |
|---|---|---|---|---|---|
| 76 | 4 | 200 mg | 3-pentyl chloroformate | 168.6 mg | 62.6 mg |
| 77 | 4 | 200 mg | cyclopropylethyl chloroformate | 170.9 mg | 230 mg |
| 78 | 4 | 200 mg | 3,3,3-trifluoropropyl chloroformate | 203 mg | 212.1 mg |
| 79 | 4 | 200 mg | 3-pentyl chlorofarmate | 168.6 mg | 220.0 mg |
| 80 | 3 | 100 mg | 2-cyanoethyl chloraformate | 72.0 mg | 81.9 mg |
| 81 | 4 | 200 mg | 2-cyanoethyl chloroformate | 153.6 mg | 214 mg |

$^1$H-NMR data of compounds 1 to 81 were as follows.

TABLE 3

| Compound No. | $^1$H-NMR data; δ (ppm) from TMS in CDCL$_3$ |
|---|---|
| 1 | 7.78 (1H, dd, J1 = 11.2 Hz, J2 = 7.6 Hz), 7.43 (1H, dd, J1 = 10.5 Hz, J2 = 8.3 Hz), 2.99 (2H, q, J = 7.6 Hz), 2.26 (3H, s), 2.06 (1H, m), 1.36 (3H, t, J = 7.5 Hz), 1.29 (2H, m), 1.18 (2H, m) |
| 2 | 7.79 (1H, m), 7.45 (1H, dd, J1 = 17.8 Hz, J2 = 9.7 Hz), 2.99 (2H, q, J = 7.6 Hz), 2.30 (3H, s), 2.01 (1H, m), 1.37 (3H, t, J = 7.6 Hz), 1.29 (2H, m), 1.13 (2H, m) |
| 3 | 7.80 (1H, m), 7.40 (1H, dd, J1 = 10.5 Hz, J2 = 8.2 Hz), 3.00 (2H, q, J = 7.5 Hz), 2.51 (3H, s), 2.67 (3H, s), 1.37 (3H, t, J = 7.5 Hz) |
| 4 | 7.78 (1H, m), 7.37 (1H, dd, J1 = 10.7 Hz, J2 = 8.3 Hz), 2.99 (2H, q, J = 7.6 Hz), 2.81 (2H, q, J = 7.5 Hz), 2.25 (3H, s), 1.40 (3H, t, J = 7.5 Hz), 1.37 (3H, t, J = 7.5 Hz) |
| 5 | 7.79 (1H, m), 7.38 (1H, dd, J1 = 10.7 Hz, J2 = 8.5 Hz), 2.99 (2H, q, J = 7.5 Hz), 2.77 (2H, t, J = 7.3 Hz), 2.25 (3H, s), 1.86 (2H, m), 1.52 (2H, m), 1.37 (3H, t, J = 7.5 Hz), 1.03 (3H, t, J = 7.3 Hz) |
| 6 | 7.80 (1H, m), 7.37 (1H, dd, J1 = 10.7 Hz, J2 = 8.6 Hz), 3.62 (1H, m), 3.00 (2H, m), 2.56 (2H, m), 2.48 (2H, m), 2.25 (3H, s), 2.15 (2H, m), 1.37 (3H, t, J = 7.6 Hz) |
| 7 | 7.79 (1H, m), 7.37 (1H, dd, J1 = 10.7 Hz, J2 = 8.2 Hz), 2.99 (2H, q, J = 7.5 Hz), 2.66 (2H, d, J = 7.1 Hz), 2.34 (1H, m), 2.26 (3H, s), 1.37 (3H, t, J = 7.6 Hz), 1.14 (6H, d, J = 6.6 Hz) |
| 8 | 7.80 (1H, dd, J1 = 11.2 Hz, J2 = 7.6 Hz), 7.50 (1H, dd, J1 = 10.5 Hz, J2 = 8.3 Hz), 4.00 (3H, s), 3.00 (2H, q, J = 7.5 Hz), 2.32 (3H, s), 1.37 (3H, t, J = 7.6 Hz) |
| 9 | 7.78 (1H, dd, J1 = 11.2 Hz, J2 = 7.5 Hz), 7.51 (1H, dd, J1 = 10.5 Hz, J2 = 8.3 Hz), 4.39 (2H, q, J = 7.0 Hz), 2.99 (2H, q, J = 7.5 Hz), 2.32 (3H, s), 1.45 (3H, t, J = 7.0 Hz), 1.37 (3H, t, J = 7.4 Hz) |
| 10 | 7.79 (1H, dd, J1 = 10.9 Hz, J2 = 7.5 Hz), 7.50 (1H, dd, J1 = 10.7 Hz, J2 = 8.3 Hz), 4.33 (2H, t, J = 6.8 Hz), 2.99 (2H, q, J = 7.5 Hz), 2.31 (3H, s), 1.78 (2H, m), 1.48 (2H, m), 1.37 (3H, t, J = 7.5 Hz), 1.00 (3H, t, J = 7.5 Hz) |
| 11 | 7.78 (1H, dd, J1 = 11.2 Hz, J2 = 7.6 Hz), 7.50 (1H, dd, J1 = 10.7 Hz, J2 = 8.5 Hz), 5.02 (1H, m), 2.99 (2H, q, J = 7.5 Hz), 2.31 (3H, s), 1.43 (6H, d, J = 6.4 Hz), 1.37 (3H, t, J = 7.5 Hz) |
| 12 | 7.81 (1H, m), 7.46 (1H, m), 2.99 (2H, q, J = 7.3 Hz), 2.45 (3H, s), 2.30 (3H, s), 1.37 (3H, t, J = 7.6 Hz) |
| 13 | 7.82 (1H, m), 7.47 (1H, dd, J1 = 17.8 Hz, J2 = 9.5 Hz), 4.33 (2H, t, J = 6.6 Hz), 3.00 (2H, q, J = 7.6 Hz), 2.36 (3H, s), 1.78 (2H, m), 1.49 (2H, m), 1.38 (3H, t, J = 7.5 Hz), 0.99 (3H, t, J = 7.3 Hz) |
| 14 | 7.83 (1H, m), 7.48 (1H, dd, J1 = 18.0 Hz, J2 = 9.7 Hz), 5.03 (1H, m), 3.00 (2H, q, J = 7.5 Hz), 1.43 (6H, d, J = 6.3 Hz), 0.73 (3H, t, J = 7.5 Hz) |
| 15 | 7.74 (1H, dd, J1 = 11.0 Hz, J2 = 7.7 Hz), 7.43 (1H, dd, J1 = 10.8 Hz, J2 = 8.6 Hz), 2.69 (3H, s), 2.23 (3H, s), 2.05 (1H, m), 1.29 (2H, m), 1.18 (2H, m) |
| 16 | 7.77 (1H, m), 7.45 (1H, m), 2.70 (3H, s), 2.28 (3H, s), 2.01 (1H, m), 1.28 (2H, m), 1.13 (2H, m) |
| 17 | 7.75 (1H, dd, J1 = 11.2 Hz, J2 = 7.5 Hz), 7.40 (1H, dd, J1 = 10.7 Hz, J2 = 8.2 Hz), 2.70 (3H, s), 2.51 (3H, s), 2.24 (3H, s) |
| 18 | 8.13 (1H, d, J = 7.1 Hz), 7.37 (1H, d, J = 9.3 Hz), 2.99 (2H, q, J = 7.4 Hz), 2.51 (3H, s), 2.27 (3H, s), 1.37 (3H, t, J = 7.6 Hz) |
| 19 | 7.98 (1H, dd, J1 = 9.3 Hz, J2 = 5.4 Hz), 7.47 (1H, t, J = 9 Hz), 3.00 (2H, q, J = 7.5 Hz), 2.48 (3H, s), 2.28 (3H, s), 1.37 (3H, t, J = 7.6 Hz) |
| 20 | 8.11 (1H, d, J = 7.1 Hz), 7.59 (1H, dd, J1 = 9.3 Hz), 2.98 (2H, q, J = 7.6 Hz), 2.26 (3H, s), 2.04 (1H, m), 1.36 (3H, t, J = 7.6 Hz), 1.29 (2H, m), 1.18 (2H, m) |
| 21 | 8.00 (1H, m), 7.46 (1H, t, J = 9.0 Hz), 2.99 (2H, q, J = 7.5 Hz), 2.29 (3H, s), 2.06 (1H, m), 1.37 (3H, t, J = 7.6 Hz), 1.27 (2H, m), 1.14 (2H, m) |

TABLE 3-continued

| | |
|---|---|
| 22 | 8.12 (1H, d, J = 7.1 Hz), 7.69 (1H, d, J = 9.2 Hz), 5.02 (1H, m), 2.99 (2H, q, J = 7.3 Hz), 2.31 (3H, s), 1.43 (6H, d, J = 6.1 Hz), 1.37 (3H, t, J = 7.5 Hz) |
| 23 | 7.98 (1H, m), 7.46 (1H, t, J = 8.9 Hz), 5.04 (1H, m), 3.00 (2H, q, J = 7.4 Hz), 2.34 (3H, s), 1.42 (6H, d, J = 6.4 Hz), 1.37 (3H, t, J = 7.5 Hz) |
| 24 | 7.83 (1H, m), 7.49 (1H, dd, J1 = 13.9 Hz, J2 = 9.8 Hz), 3.99 (3H, s), 3.00 (2H, t, J = 7.3 Hz), 2.37 (3H, s), 1.38 (3H, t, J = 7.5 Hz) |
| 25 | 7.81 (1H, m), 7.49 (1H, dd, J1 = 17.7 Hz, J2 = 9.5 Hz), 3.99 (3H, s), 2.71 (3H, s), 2.34 (3H, s) |
| 26 | 8.09 (1H, d, J = 7.0 Hz), 7.42 (1H, d, J = 9.3 Hz), 2.70 (3H, s), 2.24 (3H, s), 2.05 (1H, m), 1.29 (2H, m), 1.18 (2H, m) |
| 27 | 7.90 (1H, m), 7.47 (1H, t, J = 8.8 Hz), 2.72 (3H, s), 2.27 (3H, s), 2.07 (1H, m), 1.28 (2H, m), 1.15 (2H, m) |
| 28 | 8.14 (1H, brs), 7.50 (1H, d, J = 9.3 Hz), 4.00 (3H, s), 2.72 (3H, s), 2.31 (3H, s) |
| 29 | 8.09 (1H, d, J = 7.0 Hz), 7.38 (1H, d, J = 9.5 Hz), 2.70 (3H, s), 2.51 (3H, s), 2.24 (3H, s) |
| 30 | 7.81 (1H, m), 7.47 (1H, dd, J1 = 18.1 Hz, J2 = 9.8 Hz), 3.00 (2H, q, J = 7.5 Hz), 2.77 (2H, q, J = 7.5 Hz), 2.29 (3H, s), 1.37 (3H, t, J = 7.5 Hz), 1.35 (3H, t, J = 7.5 Hz) |
| 31 | 7.82 (1H, m), 7.46 (1H, dd, J1 = 18.2 Hz, J2 = 9.3 Hz), 3.56 (1H, m), 3.00 (2H, m), 2.57 (2H, m), 2.42 (2H, m), 2.28 (3H, s), 2.10 (2H, m), 1.37 (3H, t, J = 7.6 Hz) |
| 32 | 7.81 (1H, m), 7.45 (1H, dd, J1 = 18.1 Hz, J2 = 9.6 Hz), 2.99 (2H, q, J = 7.3 Hz), 2.63 (2H, d, J = 7.0 Hz), 2.32 (1H, m), 2.30 (3H, s), 1.37 (3H, t, J = 7.6 Hz), 1.11 (6H, d, J = 6.8 Hz) |
| 33 | 7.83 (1H, m), 7.49 (1H, dd, J1 = 18.0 Hz, J2 = 9.7 Hz), 4.40 (2H, q, J = 7.1), 3.01 (2H, q, J = 7.6 Hz), 2.37 (3H, s), 1.44 (3H, t, J = 7.2 Hz), 1.38 (3H, t, J = 7.6 Hz) |
| 34 | 7.79 (1H, m), 7.40 (1H, dd, J1 = 10.7 Hz, J2 = 8.4 Hz), 3.40 (1H, m), 2.28 (3H, s), 2.03 (1H, m), 1.35 (6H, d, J = 6.6 Hz), 1.18 (2H, m), 1.13 (2H, m) |
| 35 | 7.83 (1H, m), 7.48 (1H, dd, J1 = 10.7 Hz, J2 = 8.5 Hz), 4.00 (3H, s), 3.41 (1H, m), 2.34 (3H, s), 1.36 (6H, d, J = 6.8 Hz) |
| 36 | 7.98 (1H, m), 7.47 (1H, t, J = 8.9 Hz), 3.99 (3H, s), 3.01 (2H, q, J = 7.4 Hz), 2.35 (3H, s), 1.38 (3H, t, J = 7.4 Hz) |
| 37 | 7.98 (1H, dd, J1 = 9.1 Hz, J2 = 5.2 Hz), 7.47 (1H, t, J = 8.9 Hz), 4.33 (2H, t, J = 6.6 Hz), 3.00 (2H, q, J = 7.5 Hz), 2.34 (3H, s), 1.77 (2H, m), 1.48 (2H, m), 1.37 (3H, t, J = 7.5 Hz), 0.98 (3H, t, J = 7.3 Hz) |
| 38 | 7.98 (1H, dd, J1 = 9.3 Hz, J2 = 5.2 Hz), 7.46 (1H, t, J = 9.0 Hz), 4.39 (2H, q, J = 7.1 Hz), 3.00 (2H, q, J = 7.5 Hz), 2.34 (3H, s), 1.43 (3H, t, J = 7.1 Hz), 1.37 (3H, t, J = 7.4 Hz) |
| 39 | 7.54 (1H, m), 7.26 (1H, dd, J1 = 18.0 Hz, J2 = 9.7 Hz), 3.11 (2H, m), 2.50 (3H, s), 2.37 (3H, s), 1.40 (3H, t, J = 7.6 Hz) |
| 40 | 7.86 (1H, m), 7.51 (1H, dd, J1 = 17.8 Hz, J2 = 9.8 Hz), 7.17 (1H, dd, J1 = 13.9 Hz, J2 = 6.1 Hz), 5.13 (1H, dd, J1 = 13.7 Hz, J2 = 2.3 Hz), 4.76 (1H, dd, J1 = 12.2 Hz, J2 = 2.5 Hz), 3.02 (2H, q, J = 7.5), 2.39 (3H, s), 1.39 (3H, t, J = 7.6) |
| 41 | 7.86 (1H, m), 7.51 (1H, dd, J1 = 17.8 Hz, J2 = 9.8 Hz), 4.92 (2H, d, J = 2.4 Hz), 3.02 (2H, q, J = 7.6 Hz), 2.63 (1H, t, J = 2.5 Hz), 2.38 (3H, s), 1.38 (3H, t, J = 7.6 Hz) |
| 42 | 7.86 (1H, m), 7.51 (1H, dd, J1 = 17.8 Hz, J2 = 9.8 Hz), 5.88 (2H, s), 3.02 (2H, q, J = 7.5 Hz), 2.37 (3H, s), 1.39 (3H, t, J = 7.6 Hz) |
| 43 | 7.85 (1H, m), 7.50 (1H, dd, J1 = 18.0 Hz, J2 = 9.8 Hz), 4.47 (2H, s), 3.01 (2H, q, J = 7.5 Hz), 2.34 (3H, s), 1.38 (3H, t, J = 7.5 Hz) |
| 44 | 7.81 (1H, m), 7.48 (1H, dd, J1 = 17.8 Hz, J2 = 9.5 Hz), 2.71 (3H, s), 2.46 (3H, s), 2.29 (3H, s) |
| 45 | 7.81 (1H, m), 7.49 (1H, dd, J1 = 17.8 Hz, J2 = 9.5 Hz), 4.40 (2H, q, J = 7.2 Hz), 2.72 (3H, s), 2.35 (3H, s), 1.44 (3H, t, J, = 7.2 Hz) |
| 46 | 7.91 (1H, m), 7.53 (1H, m), 2.76 (3H, brs), 2.50 (3H, s), 2.34 (3H, s) |
| 47 | 7.48 (1H, m), 7.49 (1H, dd, J1 = 18.0 Hz, J2 = 9.8 Hz), 6.73 (1H, dd, J1 = 17.3 Hz, J2 = 1.3 Hz), 6.46 (1H, dd, J1 = 9.3 Hz, J2 = 10.5 Hz), 6.16 (1H, dd, J1 = 10.6 Hz, J2 = 1.1 Hz), 3.02 (2H, q, J = 7.5 Hz), 2.31 (3H, s), 1.38 (3H, t, J = 7.6 Hz) |
| 48 | 7.82 (1H, m), 7.48 (1H, dd, J1 = 18.0 Hz, J2 = 9.8 Hz), 3.00 (3H, m), 2.29 (3H, s), 1.43 (6H, d, J = 7.1 Hz), 1.37 (3H, t, J = 7.6 Hz) |
| 49 | 7.81 (1H, m), 7.49 (1H, dd, J1 = 18.0 Hz, J2 = 9.5 Hz), 2.71 (3H, s), 2.26 (3H, s), 2.14 (1H, m), 2.04 (1H, m), 1.69 (3H, brd) |
| 50 | 7.86 (1H, m), 7.52 (1H, m), 4.92 (2H, d, J = 2.4 Hz), 2.74 (3H, s), 2.63 (1H, t, J = 2.5 Hz), 2.36 (3H, s) |
| 51 | 7.82 (1H, m), 7.51 (1H, dd, J1 = 17.8 Hz, J2 = 9.5 Hz), 7.17 (1H, dd, J1 = 13.9 Hz, J2 = 6.1 Hz), 5.13 (1H, dd, J1 = 13.8 Hz, J2 = 2.4 Hz), 4.76 (1H, dd, J1 = 6.1 Hz, J2 = 2.2 Hz), 2.72 (3H, s), 2.36 (3H, s) |
| 52 | 7.80 (1H, m), 7.49 (1H, dd, J1 = 17.8 Hz, J2 = 9.7 Hz), 4.44 (2H, t, J = 7.0 Hz), 2.71 (2H, m), 2.71 (3H, s), 2.35 (3H, s), 2.07 (1H, t, J = 2.5 Hz) |
| 53 | 7.81 (1H, m), 7.71 (1H, d, J = 13.6 Hz), 7.49 (1H, dd, J1 = 17.9 Hz, J2 = 9.7 Hz), 6.57 (1H, d, J = 13.7 Hz), 2.87 (3H, s), 2.28 (3H, s) |

TABLE 3-continued

| | |
|---|---|
| 54 | 7.80 (1H, m), 7.48 (1H, dd, J1 = 17.8 Hz, J2 = 9.5 Hz), 7.04 (1H, d, J = 8.3 Hz), 6.59 (1H, d, J = 8.3 Hz), 2.88 (3H, s), 2.28 (3H, s) |
| 55 | 7.81 (1H, m), 7.48 (1H, dd, J1 = 17.8 Hz, J2 = 9.5 Hz), 2.99 (4H, m), 2.33 (3H, s), 1.77 (2H, m), 1.37 (3H, t, J = 7.6 Hz), 1.05 (3H, t, J = 7.3 Hz) |
| 56 | 7.83 (1H, m), 7.49 (1H, dd, J1 = 17.7 Hz, J2 = 9.7 Hz), 4.44 (2H, t, J = 6.9 Hz), 3.00 (2H, q, J = 7.5 Hz), 2.71 (2H, m), 2.06 (1H, t, J = 2.7 Hz), 1.57 (3H, s), 1.38 (3H, t, J = 7.5 Hz) |
| 57 | 7.80 (1H, m), 7.49 (1H, dd, J1 = 17.8 Hz, J2 = 9.7 Hz), 6.03 (1H, m), 5.47 (1H, dd, J1 = 17.2 Hz, J2 = 1.4 Hz), 5.38 (1H, dd, J1 = 10.3 Hz, J2 = 1.1 Hz), 4.82 (2H, d, J = 5.8 Hz), 2.71 (3H, s), 2.35 (3H, s) |
| 58 | 7.79 (1H, m), 7.49 (1H, dd, J1 = 17.8 Hz, J2 = 9.5 Hz), 2.91 (2H, t, J = 7.6 Hz), 2.70 (3H, s), 2.41 (2H, dt, J1 = 6.8 Hz, J2 = 2.7 Hz), 2.28 (3H, s), 2.05 (3H, m) |
| 59 | 7.80 (1H, m), 7.48 (1H, dd, J1 = 17.8 Hz, J2 = 9.5 Hz), 3.00 (2H, t, J = 7.3 Hz), 2.71 (2H, m), 2.70 (3H, s), 2.30 (3H, s), 2.07 (1H, m) |
| 60 | 7.82 (1H, m), 7.50 (1H, m), 3.62 (2H, brs), 2.72 (3H, brs), 2.30 (3H, brs) |
| 61 | 8.18 (1H, dd, J1 = 9.2 Hz, J2 = 4.9 Hz), 7.43 (1H, dd, J1 = 13.0 Hz, J2 = 10.6 Hz), 2.71 (3H, s), 2.24 (3H, s), 2.05 (1H, m), 1.19 (2H, m), 1.11 (2H, m) |
| 62 | 8.20 (1H, dd, J1 = 9.3 Hz, J2 = 4.9 Hz), 7.45 (1H, dd, J1 = 13.2 Hz, J2 = 10.7 Hz), 3.96 (3H, s), 2.73 (3H, s), 2.32 (3H, s) |
| 63 | 8.33 (1H, d, J = 6.6 Hz), 7.46 (1H, d, J = 10.8 Hz), 2.73 (3H, s), 2.28 (3H, s), 2.07 (1H, m), 1.30 (2H, m), 1.20 (2H, m) |
| 64 | 8.34 (1H, d, J = 6.6 Hz), 7.55 (1H, d, J = 10.7 Hz), 4.01 (3H, s), 2.74 (3H, s), 2.35 (3H, s) |
| 65 | 7.88 (1H, d, J = 9.0 Hz), 7.68 (1H, d, J = 9.0 Hz), 2.70 (3H, s), 2.48 (3H, s), 2.26 (3H, s) |
| 66 | 7.87 (1H, d, J = 9.0 Hz), 7.67 (1H, d, J = 9.0 Hz), 2.70 (3H, s), 2.26 (3H, s), 2.07 (1H, m), 1.27 (2H, m), 1.14 (2H, m) |
| 67 | 7.88 (1H, d, J = 9.1 Hz), 7.69 (1H, d, J = 9.1 Hz), 3.99 (3H, s), 2.71 (3H, s), 2.33 (3H, s) |
| 68 | 8.13 (1H, s), 7.78 (1H, s), 2.70 (3H, s), 2.52 (3H, s), 2.24 (3H, s) |
| 69 | 8.12 (1H, s), 7.81 (1H, s), 2.70 (3H, s), 2.24 (3H, s), 2.08 (1H, m), 1.30 (2H, m), 1.20 (1H, m) |
| 70 | 8.14 (1H, s), 7.90 (1H, s), 4.01 (3H, s), 2.71 (3H, s), 2.30 (3H, s) |
| 71 | 7.83 (1H, m), 7.48 (1H, dd, J1 = 18.0 Hz, J2 = 9.5 Hz), 4.41 (2H, t, J = 6.8 Hz), 3.00 (2H, q, J = 7.6 Hz), 2.37 (3H, s), 1.69 (2H, q, J = 6.9 Hz), 1.38 (3H, t, J = 7.5), 0.80 (1H, m), 0.52 (2H, m), 0.15 (2H, m) |
| 72 | 7.84 (1H, m), 7.50 (1H, dd, J1 = 18.0 Hz, J2 = 9.5 Hz), 4.56 (2H, t, J = 6.4 Hz), 3.01 (2H, q, J = 7.5 Hz), 2.65 (2H, m), 2.36 (3H, s), 1.38 (3H, t, J = 7.6 Hz) |
| 73 | 7.83 (1H, m), 7.48 (1H, dd, J1 = 18.0 Hz, J2 = 9.5 Hz), 4.39 (2H, t, J = 7.0 Hz), 3.00 (2H, q, J = 7.5 Hz), 2.64 (2H, m), 2.37 (3H, s), 1.80 (3H, t, J = 2.6 Hz), 1.38 (3H, t, J = 7.6 Hz) |
| 74 | 7.80 (1H, m), 7.49 (1H, dd, J1 = 18.0 Hz, J2 = 9.7 Hz), 4.41 (2H, t, J = 6.7 Hz), 2.71 (3H, s), 2.35 (3H, s), 1.69 (2H, q, J = 6.8 Hz), 0.80 (1H, m), 0.52 (2H, m), 0.41 (2H, m) |
| 75 | 7.81 (1H, m), 7.50 (1H, dd, J1 = 18.0 Hz, J2 = 9.5 Hz), 4.56 (2H, t, J = 6.4 Hz), 2.71 (3H, s), 2.65 (2H, m), 2.34 (3H, s) |
| 76 | 7.80 (1H, m), 7.49 (1H, dd, J1 = 18.0 Hz, J2 = 9.7 Hz), 4.39 (2H, t, J = 7.1 Hz), 2.71 (3H, s), 2.64 (2H, m), 2.35 (3H, s), 1.81 (3H, t, J = 2.6 Hz) |
| 77 | 7.76 (1H, dd, J1 = 11.2 Hz, J2 = 7.5 Hz), 7.53 (1H, dd, J1 = 10.4 Hz, J2 = 8.3 Hz), 4.41 (2H, t, J = 6.7 Hz), 2.70 (3H, s), 2.30 (3H, s), 1.69 (2H, q, J = 6.8 Hz), 0.80 (1H, m), 0.53 (2H, m), 0.17 (2H, m) |
| 78 | 7.77 (1H, dd, J1 = 11.2 Hz, J2 = 7.6 Hz), 7.49 (1H, dd, J1 = 10.5 Hz, J2 = 8.3 Hz), 4.57 (2H, t, J = 6.1 Hz), 2.71 (3H, s), 2.65 (2H, m), 2.29 (3H, s) |
| 79 | 7.76 (1H, dd, J1 = 11.2 Hz, J2 = 7.5 Hz), 7.55 (1H, dd, J1 = 10.5 Hz, J2 = 8.3 Hz), 4.39 (2H, t, J = 6.7 Hz), 2.70 (3H, s), 2.65 (2H, m), 2.31 (3H, s), 1.82 (3H, t, J = 2.4 Hz) |
| 80 | 7.85 (1H, m), 7.50 (1H, dd, J1 = 18.0 Hz, J2 = 9.5 Hz), 4.54 (2H, t, J = 6.4 Hz), 3.01 (2H, q, J = 7.5 Hz), 2.89 (2H, t, J = 6.5 Hz), 2.38 (3H, s), 1.38 (3H, t, J = 7.6 Hz) |
| 81 | 7.76 (1H, dd, J1 = 11.0 Hz, J2 = 7.5 Hz), 7.51 (1H, dd, J1 = 10.5 Hz, J2 = 8.3 Hz), 4.54 (2H, t, J = 6.3 Hz), 2.89 (2H, t, J = 6.3 Hz), 2.71 (3H, s), 2.31 (3H, s) |

Preparation Example 1: WP (wettable powder) preparation

| | |
|---|---|
| Compound 2 | 25 wt% |
| Sodium diisobutylnaphthalenesulfonate | 1 wt% |
| Calcium n-dodecylbenzenesulfonate | 10 wt% |
| Alkylaryl polyglycol ether | 12 wt% |
| Sodium salt of naphthalenesulfonic acid formalin condensate | 3 wt% |

TABLE 3-continued

| | |
|---|---|
| Emulsion-type silicone | 1 wt% |
| Silicon dioxide | 3 wt% |
| Kaolin | 45 wt% |

Preparation Example 2: Water-soluble concentrate preparation

| | |
|---|---|
| Compound 2 | 20 wt% |
| Polyoxyethylene lauryl ether | 3 wt% |
| Sodium dioctylsulfosuccinate | 3.5 wt% |
| Dimethyl sulfoxide | 37 wt% |
| 2-Propanol | 36.5 wt% |

Preparation Example 3: Liquid preparation for spray

| | |
|---|---|
| Compound 2 | 2 wt% |
| Dimethyl sulfoxide | 10 wt% |
| 2-Propanol | 35 wt% |
| Acetone | 53 wt% |

Preparation Example 4: Liquid preparation for percutaneous administration

| | |
|---|---|
| Compound 1 | 5 wt% |
| Hexylene glycol | 50 wt% |
| Isopropanol | 45 wt% |

Preparation Example 5: Liquid preparation for percutaneous administration

| | |
|---|---|
| Compound 2 | 5 wt% |
| Propylene glycol monomethyl ether | 50 wt% |
| Dipropylene glycol | 45 wt% |

Preparation Example 6: Liquid preparation for percutaneous (pour-on) administration

| | |
|---|---|
| Compound 2 | 2 wt% |
| Light liquid paraffin | 98 wt% |

Preparation Example 7: Liquid preparation for percutaneous (pour-on) administration

| | |
|---|---|
| Compound 2 | 2 wt% |
| Light liquid paraffin | 58 wt% |
| Olive oil | 30 wt% |
| ODO-H | 9 wt% |
| Shin-Etsu silicone | 1 wt% |

Test Example 1

Miticidal Effect Against *Ornithonyssus Sylviarum*

The tip of a Pasteur pipette was sealed with Parafilm, and a sample compound diluted with acetone to 50 ppm was poured into the pipette from its top. The Parafilm in the tip of the pipette was removed one min after the pouring to discharge the test solution, and the pipette was air dried. Thereafter, an absorbent cotton was inserted into the upper end of the pipette, and 10 sucking adult mites of *Ornithonyssus sylviarum* were released in the pipette. The tip of the pipette was sealed with Hematoseal, and the pipette was then placed in a desiccator containing a saturated ammonium sulfate solution in its bottom and was stored under fully darkened conditions at 25° C. The mites were observed under a stereomicroscope 24 hr after the treatment to judge whether the mites were dead or survived, followed by determination of the death rate (%). The results are shown below.

| Compound No. | Concentration | Death rate, % |
|---|---|---|
| 1 | 50 ppm | 80 |
| 2 | 50 ppm | 100 |

-continued

| Compound No. | Concentration | Death rate, % |
|---|---|---|
| 12 | 50 ppm | 100 |
| 14 | 50 ppm | 100 |
| 16 | 50 ppm | 80 |
| 19 | 50 ppm | 100 |
| 21 | 50 ppm | 100 |
| 24 | 50 ppm | 100 |
| 25 | 50 ppm | 100 |

Test Example 2

Insecticidal Effect Against *Ctenocephalides felis*

Test compound solutions (0.5 ml) prepared by dissolving a test compound in acetone and diluting the solutions with acetone to designated concentrations were placed respectively in glass tubes (inner diameter 2.6 cm, height 12 cm), and acetone was evaporated at room temperature to form a dry film of the test compound at the bottom of each glass tube. Non-sucking adult fleas (10 heads) of *Ctenocephalides felis* were released in the glass tubes. The glass tubes were then lidded. Whether the fleas were dead or survived was judged 24 hr after the initiation of rearing. The death rate (%) was determined from the number of dead fleas. Rearing was carried out at a temperature of 25° C. and a relative humidity of 90% under fully darkened conditions. The test was repeated three times. The test results are shown below.

| Compound No. | Concentration | Death rate (%) |
| --- | --- | --- |
| 2 | 20 ppm | 100 |
| 2 | 4 ppm | 97 |
| 24 | 20 ppm | 100 |
| 24 | 4 ppm | 84 |
| 1 | 20 ppm | 100 |
| 19 | 4 ppm | 100 |
| 39 | 4 ppm | 80 |
| 52 | 4 ppm | 70 |

Test Example 3

Tickcidal Effect Against *Haemaphysalis longicornis*

A test compound solution (1.0 ml) prepared by dissolving a test compound in acetone and diluting the solution with acetone to 10 ppm was dropped on a glass Schale having a diameter of 9 cm. Acetone was evaporated at room temperature to form a dry film of the test compound at the bottom of the Schale. Larva ticks of *Haemaphysalis longicornis* (40 to 100 head) were released in the Petri dish, and the Schale was then lidded and was hermetically sealed by covering with a polyethylene sheet. Rearing was carried out at a temperature of 25° C. and a relative humidity of 100% under fully darkened conditions. The number of ticks, which have fallen on their side, was counted 24 hr after the initiation of rearing. The death rate (%) was determined from the number of dead ticks. The test was repeated twice. The test results are shown below.

| Compound No. | Concentration | Death rate, % |
| --- | --- | --- |
| 2 | 10 ppm | 100 |
| 16 | 10 ppm | 100 |
| 24 | 10 ppm | 100 |
| 25 | 10 ppm | 100 |
| 30 | 10 ppm | 100 |
| 39 | 10 ppm | 100 |
| 41 | 10 ppm | 100 |
| 44 | 10 ppm | 100 |
| 46 | 10 ppm | 100 |
| 50 | 10 ppm | 100 |
| 52 | 10 ppm | 100 |
| 56 | 10 ppm | 100 |

Test Example 4

Miticidal Effect Against *Dermanyssus gallinae*

The tip of a Pasteur pipette was sealed with Parafilm, and a sample compound diluted with acetone to 50 ppm was poured into the pipette from its top. The Parafilm in the tip of the pipette was removed one min after the pouring to discharge the test solution, and the pipette was air dried. Thereafter, an absorbent cotton was inserted into the upper end of the pipette, and 10 sucking adult mites of *Dermanyssus gallinae* were released in the pipette. The tip of the pipette was sealed with Hematoseal, and the pipette was then placed in a desiccator containing a saturated ammonium sulfate solution in its bottom and was stored under fully darkened conditions at 25° C. The mites were observed under a stereomicroscope 24 hr after the treatment to judge whether the mites were dead or survived, followed by determination of the death rate of mites (%). The results are shown below.

| Compound No. | Concentration | Death rate, % |
| --- | --- | --- |
| 2 | 50 ppm | 100 |
| 12 | 50 ppm | 95 |
| 13 | 50 ppm | 85 |
| 16 | 50 ppm | 100 |
| 24 | 50 ppm | 100 |
| 25 | 50 ppm | 100 |
| 30 | 50 ppm | 100 |
| 33 | 50 ppm | 100 |
| 39 | 50 ppm | 100 |
| 41 | 50 ppm | 100 |
| 44 | 50 ppm | 100 |
| 45 | 50 ppm | 100 |
| 46 | 50 ppm | 100 |
| 47 | 50 ppm | 100 |
| 48 | 50 ppm | 100 |
| 50 | 50 ppm | 95 |
| 51 | 50 ppm | 90 |
| 52 | 50 ppm | 100 |
| 53 | 50 ppm | 100 |
| 54 | 50 ppm | 100 |
| 55 | 50 ppm | 100 |
| 56 | 50 ppm | 95 |
| 57 | 50 ppm | 100 |
| 58 | 50 ppm | 80 |
| 62 | 50 ppm | 100 |
| 65 | 50 ppm | 80 |
| 67 | 50 ppm | 100 |

The invention claimed is:

1. A compound represented by formula (I) or a salt thereof:

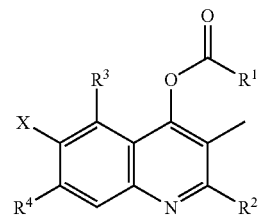

(I)

wherein

R$^1$ represents alkyl having 1 to 6 carbon atoms optionally substituted by a halogen atom or cyano; alkenyl having 2 to 6 carbon atoms optionally substituted by a halogen atom or cyano; alkynyl having 2 to 6 carbon atoms optionally substituted by a halogen atom or cyano; group —O—R$^5$ wherein R$^5$ represents alkyl having 1 to 6 carbon atoms optionally substituted by a halogen atom or cyano, alkenyl having 2 to 6 carbon atoms optionally substituted by a halogen atom or cyano, or alkynyl having 2 to 6 carbon atoms optionally substituted by a halogen atom or cyano; or group —S—R$^5$ wherein R$^5$ is as defined above, R$^2$ represents alkyl having 1 to 4 carbon atoms optionally substituted by a halogen atom, any one of R³ and R⁴ represents a hydrogen atom and the other represents a fluorine atom, a chlorine atom, a bromine atom, or —CF₃, and X represents a fluorine atom or a chlorine atom.

2. The compound according to claim 1, represented by formula (Ia):

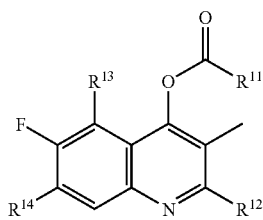

wherein R¹¹ represents alkyl having 1 to 4 carbon atoms optionally substituted by a halogen atom or alkoxy having 1 to 4 carbon atoms optionally substituted by a halogen atom; R¹² represents alkyl having 1 to 4 carbon atoms optionally substituted by a halogen atom; and any one of R¹³ and R¹⁴ represents a hydrogen atom and the other represents a fluorine or chlorine atom.

3. The compound according to claim 1, selected from the group consisting of:

(2) 2-ethyl-3-methyl-4-cyclopropanecarbonyloxy-5,6-difluoroquinoline;

(19) 2-ethyl-3-methyl-4-acetyloxy-5-chloro-6-fluoroquinoline;

(24) 2-ethyl-3-methyl-4-methoxycarbonyloxy-5,6-difluoroquinoline;

(25) 2,3-dimethyl-4-methoxycarbonyloxy-5,6-difluoroquinoline;

(39) 2-ethyl-3-methyl-4-methanethiolcarbonyloxy-5,6-difluoroquinoline;

(41) 2-ethyl-3-methyl-4-propargyloxycarbonyloxy-5,6-difluoroquinoline;

(44) 2,3-dimethyl-4-acetoxy-5,6-difluoroquinoline;

(46) 2,3-dimethyl-4-methanethiolcarbonyloxy-5,6-difluoroquinoline;

(50) 2,3-dimethyl-4-propargyloxycarbonyloxy-5,6-difluoroquinoline;

(52) 2,3-dimethyl-4-(3-butynyl)oxycarbonyloxy-5,6-difluoroquinoline;

(56) 2-ethyl-3-methyl-4-(3-butynyl)oxycarbonyloxy-5,6-difluoroquinoline;

(57) 2,3-dimethyl-4-allyloxycarbonyloxy-5,6-difluoroquinoline;

(65) 2,3-dimethyl-4-acetoxy-5,6-dichloroquinoline; and

(67) 2,3-dimethyl-4-methoxycarbonyloxy-5,6-dichloroquinoline.

4. An ectoparasite control agent composition for mammals and birds, comprising as an active ingredient the compound according to claim 1 and a suitable additive, emulsifier, excipient, adjuvant, solvent, or a carrier or a combination thereof.

5. A method for controlling an ectoparasite, comprising the step of administering an effective amount of the compound according to claim 1 to a mammal or a bird.

6. The control agent composition according to claim 4, wherein the ectoparasite is selected from the group consisting of *Anoplura*, *Siphonaptera*, and *Mesostigmata*.

7. The method according to claim 5, wherein the ectoparasite is selected from the group consisting of *Anoplura*, *Siphonaptera*, and *Mesostigmata*.

* * * * *